US006537802B1

(12) United States Patent
Alocilja et al.

(10) Patent No.: US 6,537,802 B1
(45) Date of Patent: Mar. 25, 2003

(54) METHOD AND APPARATUS FOR THE DETECTION OF VOLATILE PRODUCTS IN A SAMPLE

(75) Inventors: Evangelyn C. Alocilja, East Lansing, MI (US); Steve A. Marquie, East Lansing, MI (US); Cynthia Meeusen, Lansing, MI (US); Spring M. Younts, Lincoln, NE (US); Daniel L. Grooms, Williamston, MI (US)

(73) Assignee: Board of Trustees of Michigan State University, East Lansing, MI (US)

( * ) Notice: Subject to any disclaimer, the term of this patent is extended or adjusted under 35 U.S.C. 154(b) by 60 days.

(21) Appl. No.: 09/593,114

(22) Filed: Jun. 12, 2000

Related U.S. Application Data
(60) Provisional application No. 60/139,952, filed on Jun. 18, 1999, and provisional application No. 60/139,993, filed on Jun. 18, 1999.

(51) Int. Cl.[7] ............................. C12M 1/34; C12Q 1/04
(52) U.S. Cl. ..................... 435/287.5; 435/34; 435/807; 436/149; 422/90
(58) Field of Search ............................. 435/29, 31, 34, 435/39, 40, 287.1, 287.4, 287.5, 807; 436/20, 24, 63, 149; 422/83, 90; 73/23.34

(56) References Cited

U.S. PATENT DOCUMENTS

| | | | |
|---|---|---|---|
| 4,884,435 A | * | 12/1989 | Ehara |
| 5,051,240 A | * | 9/1991 | Nakai et al. |
| 5,407,829 A | * | 4/1995 | Wolfbeis |
| 5,571,401 A | * | 11/1996 | Lewis et al. |
| 5,621,162 A | * | 4/1997 | Yun et al. |
| 5,753,285 A | * | 5/1998 | Horan |
| 5,807,701 A | * | 9/1998 | Payne et al. |
| 5,814,474 A | | 9/1998 | Berndt |
| 5,928,609 A | | 7/1999 | Gibson et al. |
| 6,017,440 A | | 1/2000 | Lewis et al. |
| 6,033,630 A | | 3/2000 | Hinton et al. |

FOREIGN PATENT DOCUMENTS

| | | | |
|---|---|---|---|
| EP | 0 286 307 A2 | * | 10/1988 |
| WO | WO-95/33991 A1 | * | 12/1995 |
| WO | WO-97/08337 A1 | * | 3/1997 |

OTHER PUBLICATIONS

Rossi et al. 'Rapid discrimination of Micrococcaceae species using semiconductor gas sensors.' J. Microbiological Methods. Vo. 24 (1995), pp. 183–190.*

Bartlett, P.N., et al., 1997: Electronic Noses and their application in the food industry. Food Technology 51: 44–48.

Figaro USA, I. Product Information Guide Figaro USA, Inc., Feb., 1996.

Gardner, J.W., et al., 1998. The prediction of bacteria type and culture growth . . . Measurement Science and Technology 9: 120–127.

Keshri, G., et al. 1998. Use of an electronic nose for the early detection and differentiation between . . . Letters in Applied Microbiology 27: 261–264 (Abstract Only).

Lane, A.J., et al. 1998. An electronic nose to detect changes in perineal odors associated with estrus in the cow. Journal of Dairy Science 81: 2145–2150.

Tuang, R.N., et al. 1999. Identification of bacterial rep–PCR geomic fingerprints using a backpropagation neural network. FEMS Microbiology Letters 177: 249–256.

Younts, S.M., et al 1999a Development of electronic nose technology as a diagnostic tool in detection and differentiation. Journal of Animal Science 77: 129 (Abstract Only—#47).

Younts, S.M., et al. 1999b. Differentiation of *Escherichia coli* 0157:H7 from non–0157:H7 *E. coli* serotypes . . . presented at Institute of Biological Eng. Jun., Charlotte, NC.

* cited by examiner

*Primary Examiner*—William H. Beisner
(74) *Attorney, Agent, or Firm*—Ian C. McLeod

(57) ABSTRACT

A method and apparatus for detection of a small amount of volatile products from a sample using a transducer which changes voltage as a function of contact of the volatile product with the transducer. The apparatus and method are used to detect spoilage of a biological material, such as a food. The apparatus is also used to detect microorganisms and in particular pathogenic microorganisms.

35 Claims, 23 Drawing Sheets

METHOD AND APPARATUS FOR THE DETECTION OF VOLATILE PRODUCTS IN A SAMPLE

CROSS-REFERENCE TO RELATED APPLICATIONS

This application is based upon Provisional Application Serial No. 60/139,952 filed Jun. 18, 1999 and No. 60/139,993 filed on Jun. 18, 1999, respectively.

BACKGROUND OF THE INVENTION (1) Field of the Invention

The present invention relates to a method and apparatus for detection of volatile products in a sample using transducers which change resistance as a function of contact of the volatile products from the sample. In particular, the present invention relates to a method for detecting spoilage or microorganisms, particularly pathogenic microorganisms, in a sample.

(2) Description of Related Art

Food safety concerns are currently impacting public health, the meat industry, and animal production agriculture. Animal agriculture has been under increasing scrutiny as a source of foodborne pathogens. There is a need to develop a new technology that can be applied to pre-harvest food safety efforts, particularly for identifying and monitoring a potential human pathogen "on the farm".

*Escherichia coli* (*E. coli*) O157:H7 has been recognized as a significant bacterial pathogen belonging to a group of enterohemorrhagic *E. coli* associated with bloody diarrhea. It is important public health concern because of its association with commonly consumed foods, such as ground beef. Infection with this organism can cause hemorrhagic colitis, hemolytic uremic syndrome, and thrombotic thrombocytopenic purpura. The association of *E. coli* O157:H7 with ground beef has led to the identification of cattle as a reservoir for the organism. Recent pre-harvest food safety efforts have emphasized identifying factors within cattle production systems for the monitoring and control of *E. coli* O157:H7.

Computer controlled gas sensor based instruments, referred to as artificial olfactory or electronic nose technology, are finding increasing application in the food industry. The sensors are designed to detect volatile compounds that result from spoilage, rancidity, or other "off" odors. Promising results have been shown when this technology was applied to differentiating between different species of bacteria and spoilage fungi.

In today's farming industry, potatoes are stored in large bins before they are shipped out to their various destinations. Disease during storage is magnified due to extended storage periods and by requiring higher storage temperatures for immediate processing of the potatoes (Varns and Glynn, 1979). Disease losses of potatoes in storage may be as high as 30% (The Grower, 1980). As potato processing contributes up to two billion dollars a year to the economy, a small percentage of disease losses represent a significant cost to the potato industry. Currently, the managers of the potato bins monitor odor and wetness at the bottom of the bin to determine rot. By the time these indicators are detected, economic losses can be significant. At the moment, nothing can be done to arrest the spread of the damage. Monitoring of volatiles arising from host-pathogen interactions could become an important early warning of potato disease problems. Disease due to *Erwinia carotovora* infection is a major problem in potato storage. *Erwinia carotovora* is a facultative anaerobic organism, in which the bacterium breaks down the structure of the vegetative cells of infected potatoes, causing soft rot. This causes a layer of wet slime to form on the outside of the potato, resulting in anaerobic conditions in the underlying cells (Costa and Loper, 1994). Varns and Glynn (1979) reported that potatoes infected with the bacterium *Erwinia carotovora* showed high levels of acetone, ethanol, and 2-butanone. Additional volatiles included acetaldehyde, methyl acetate, ethyl acetate, propanethiol, hydrogen sulfide, methyl sulfide, methyl disulfide, n-propanol, and isobutanol (Varns and Glynn, 1979). Waterer and Pritchard (1984) reported methanol, acetaldehyde, ethanol, 2-propanol, acetone, 1-propanol, and 1-butanol in the headspace of *E. carotovora* var. *carotovora* infected Russet Burbank potato tubers. These volatiles can be produced from intermediates as well as the end-product (pyruvate) of the Embden-Meyerhof pathway (Metzler, 1977).

The sense of smell has long been used as a diagnostic tool by medical professionals, law enforcement, food handlers, and countless others in everyday life. The human nose contains approximately 50 million cells in the olfactory epithelium that act as primary receptors to odorous molecules (Gardner et a., 1990; Vandendorpe, 1998). This parallel architecture led to the construction of the electronic nose, which mimics the biological system. The electronic nose is a state-of-the-art technology that can be used to provide rapid and continuous monitoring of a wide array of different volatile compounds. The term "electronic nose" is applied to an array of chemical sensors, where each sensor has only partial specificity to a wide range of odorant molecules (Bartless et al., 1997). By mapping the sensitivity of the sensors to different chemicals, a complex odor can be "fingerprinted" and identified (Lipman, 1998). The primary receptors in the biological system are replaced by an array of transducers, such as metal oxide films, that respond to a broad range of chemical vapors or odors. Electronic nose instrumentation has advanced rapidly during the past ten years, the majority of application being within the food and drink industries (Gardner and Bartlett, 1992; Kress-Rogers, 1997). Research is being done on the applications of the electronic nose in human healthcare, particularly in the identification of infection (Doctor's Guide to Medical & Other News. "Electronic Nose Sniffs out Infection"). The instrument has also been successfully applied to detect vapors (Gardner et al., 1990; Keller et al., 1994) and aviation fuels (Lauf and Hoffheins, 1990). Application in microbial detection has been reported for *Clostridium perfringes*, *Proteus*, *Haemophilus influenzae*, *Bacteriodes fragilis*, *Oxford staphylococcus*, *Pseudomonas aeruginosa* (craven et a., 1994), *Staphylococcus aureus*, and *E. coli* (Gardner et al., 1998). U.S. Pat. No. 5,807,701 to Payne et al and U.S. Pat. No. 6,017,440 to Lewis et al describe apparatus for detecting microorganisms. These patents describe different types of sensors (transducers). These methods use an array of sensors for detection.

SUMMARY OF THE INVENTION

The present invention relates to an apparatus for detection of a volatile product in a sample which comprises: a circuit comprising a transducer means mounted in a confined space for containing the sample which detects the volatile product produced from the sample to produce an analog signal; an analog to digital conversion means in the circuit for converting the analog signal to a digital signal; and acquisition means in the circuit which stores the digital signal resulting from the analog signal, in memory as a detectable signal and retrieves the detectable signal to provide the detection of the volatile product wherein the volatile product in the confined space is detected over time to produce a distinctive signature. The present invention is particularly used to detect pathogenic E. coli and salmonella sp.

Further, the present invention relates to a method for detecting a volatile product in a sample providing an apparatus adjacent the sample which comprises: a circuit comprising a transducer means mounted in the confined space for containing the sample which detects the volatile product produced from the sample to produce an analog signal; an analog to digital conversion means in the circuit for converting the analog signal to a digital signal; an acquisition means in the circuit which stores the digital signal resulting from the analog signal in a memory as a detectable signal and retrieves the detectable signal to provide detection of the volatile product; and detecting the product in the sample with the transducer means in the circuit wherein the volatile product in the confined space is detected over time to produce a distinctive signature.

Further, the present invention relates to an apparatus for the detection of a volatile by-product produced by a microorganism as a result of spoilage of a food material which comprises: a circuit comprising a transducer means mounted in a confined space containing a sample of the food material which detects the by-product produced by the microorganism to produce an analog signal; an analog to digital converter means in the circuit for converting the analog signal to a digital signal; and acquisition means in the circuit which stores from the digital signal resulting from the analog signal in a memory as a detectable signal, and retrieves the detectable signal to produce the detection of the volatile by-product wherein the volatile by-product is detected over time to produce a distinctive signature.

Further, the present invention relates to a method for detecting a volatile by-product produced by a microorganism as a result of spoilage of a biological material which comprises: providing an apparatus for the detection of a volatile by-product produced by a microorganism which comprises: a circuit comprising a transducer means mounted in a container for containing the sample which detects the by-product produced by the microorganism to produce an analog signal; an analog to digital converter means in the circuit for converting the analog signal to a digital signal; and acquisition means in the circuit which stores the digital signal resulting from the analog signal in memory as a detectable signal and retrieves the detectable signal to provide the detection of the by-product; and detecting the volatile by-product of the microorganism with the transducer means in the circuit, wherein the volatile by-product in the confined space is detected over time to produce a distinctive signature.

OBJECTS

It is therefore an object of the present invention to provide an apparatus and method for the detection of very small amounts of a volatile product (less than $10^{-1}$) parts of a volatile material per part by volume of an atmosphere around a sample. In particular, the present invention provides a detecting apparatus which uses artificial intelligence in the form of a neural network to detect a signature showing the presence of the volatile material in a sample. Further still, it is an object of the present invention to provide an apparatus and method for the detection of harmful microorganisms by measuring volatile products produced by the microorganism. Further, it is an object of the present invention to provide an apparatus and method for the detection of spoilage by-products produced by microorganisms or degradative oxidation in foods and other biological materials.

These and other objects will become increasingly apparent by reference to the following description and the drawings.

DESCRIPTION OF PREFERRED EMBODIMENTS

Rapid and economical detection of human pathogens in animal and food production systems would enhance food safety efforts. The objective of this invention is to provide a gas sensor based instrument, coupled with an artificial neural network (ANN), which is capable of differentiating the human pathogen *E. coli* O157:H7 from non-O157:H7 *E. coli* isolates. The production of gases from eight laboratory isolates and 20 field isolates of *E. coli* were monitored during growth in laboratory conditions, and a unique gas signature for each isolate was generated. An ANN was used to analyze the gas signatures, and classify the bacteria as O157:H7 or non-O157:H7 *E. coli*. Detectable differences were observed between the gas signatures of the *E. coli* O157:H7 and non-O157:H7 isolates and the ANN classified the isolates with a high degree of accuracy. Based on this work, gas sensor based technology has promise as a diagnostic tool for pathogen detection in pre-harvest and post-harvest food safety.

EXAMPLE 1

Development and Evaluation of Gas Sensor Based Instrument for Identifying *E. Coli* O157:H7 in a Laboratory Setting To reduce the incidence of human exposure to this foodborne pathogen, it is important to establish monitoring and control strategies throughout meat production and processing (Buchanan and Doyle, 1997). Currently, there is still a need for research focused on the ecological association of *E. coli* O157:H7 with cattle and production facilities (Hancock et al., 1998; Hancock et al., 1997). Methods to easily monitor *E. coli* O157:H7 "on the farm" are important for the development and evaluation of intervention strategies to control this organism.

Metabolic and physiological differences between strains of bacteria allow for their selection and identification in current culturing methods (Doyle et al., 1997; Moat and Foster, 1995). Many of these methods are based on the ability of inability of the organism to breakdown or ferment specific compounds. In the present invention, differences in the breakdown products produced by certain bacteria are detectable by monitoring their gas emissions during growth. Volatile compounds can be monitored using artificial olfactory technology based on gas sensors (Bartlett et al., 1997; Gardner et al., 1998). The objective of this Example 1 was to develop and evaluate a gas sensor based instrument capable of detecting and differentiating *E. coli* O157:H7 from non-O157:H7 *E. coli* isolates through gas emissions in laboratory cultures.

Materials and Methods
Instrumentation

Figures 1, 1A:
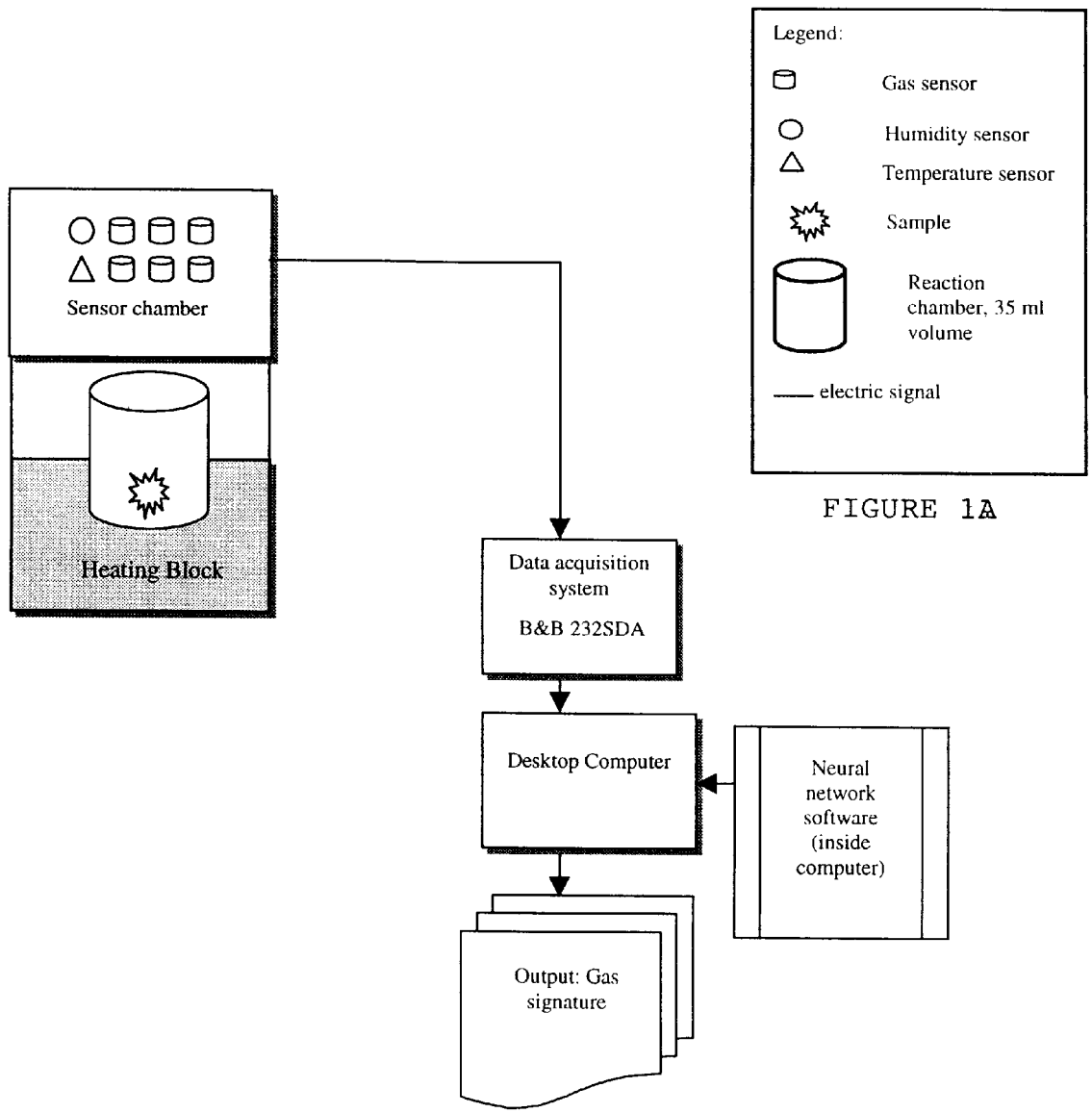
FIGS. 1 and 1C are schematics of the apparatus of the present invention for microorganism detection.
FIG. 1A is a chart showing the legends for FIG. 1.
Figure 1C:
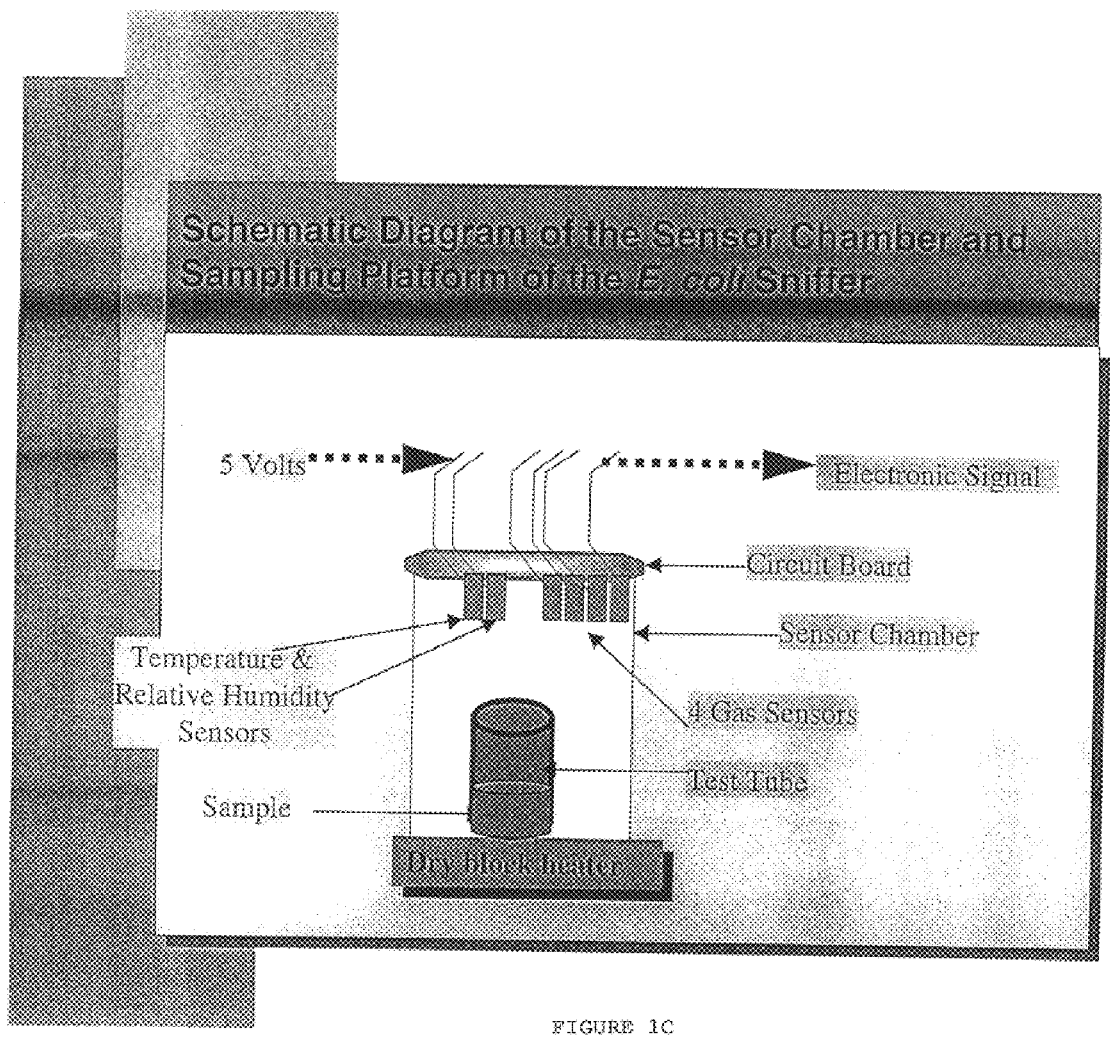
Figure 2:
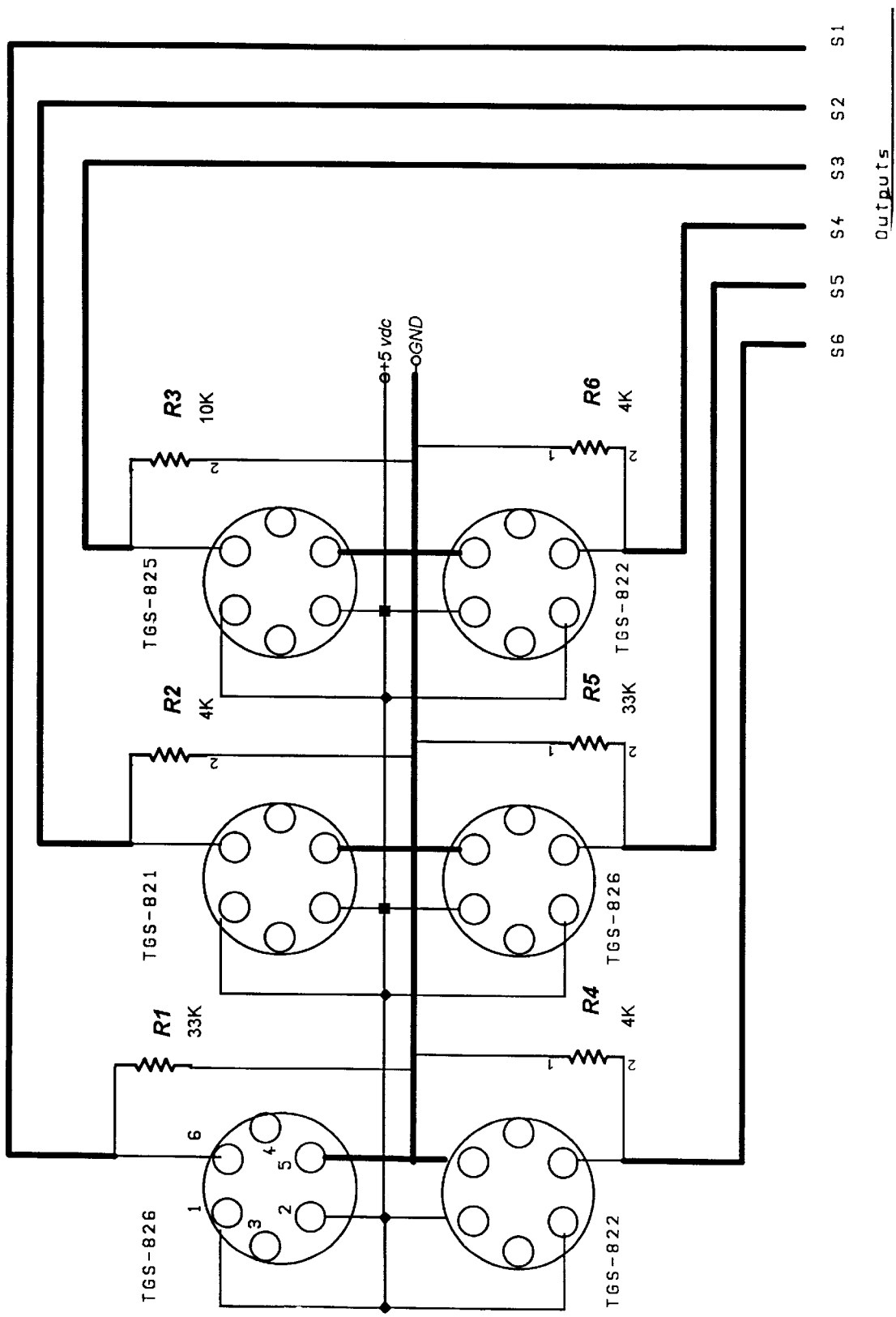
FIG. 2 is a schematic showing the sensor circuit.
Figure 2A:
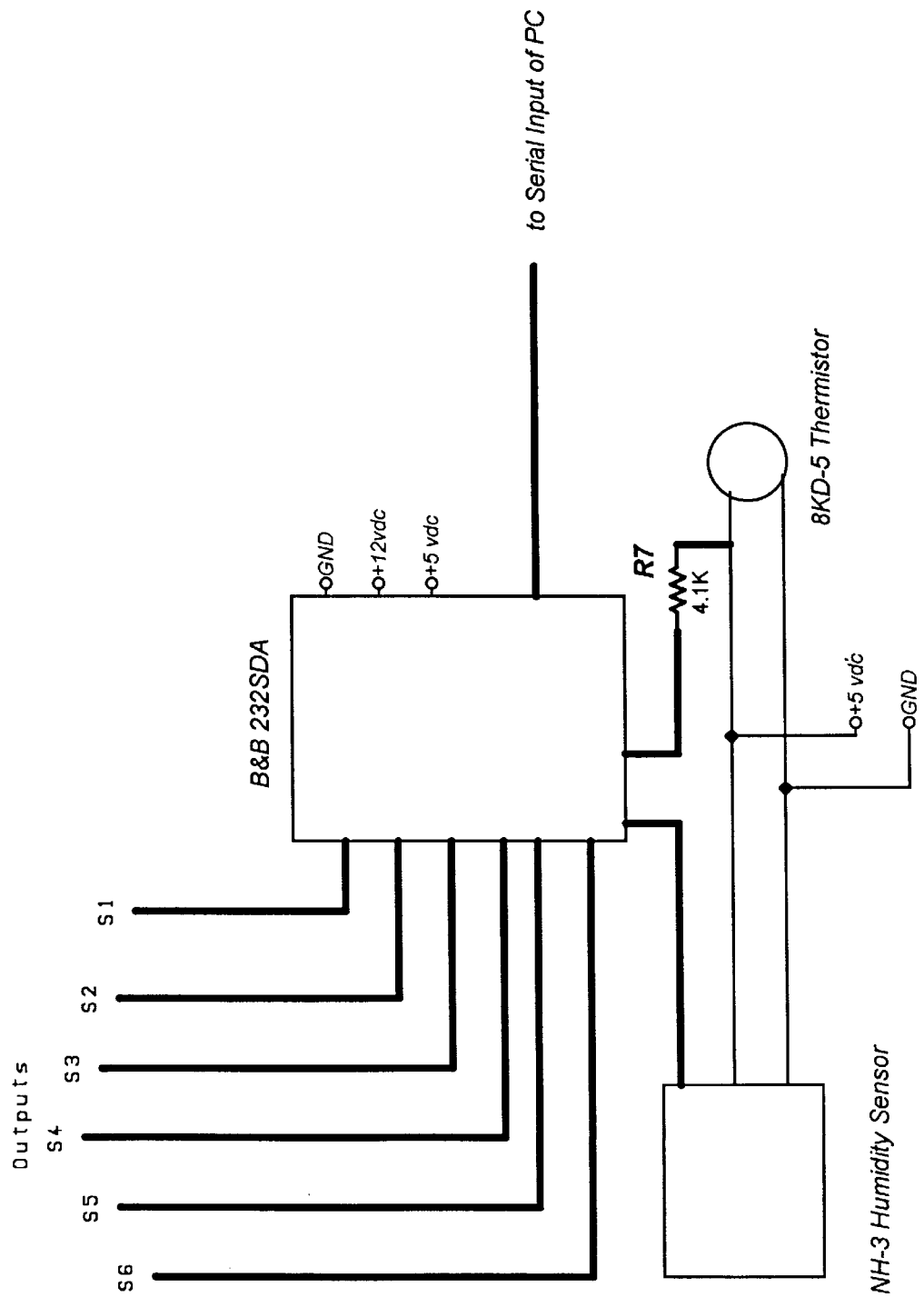
FIG. 2A is a schematic diagram showing the A/D converter circuit of FIG. 1.

An instrument was assembled for collecting, monitoring, and recording the gas emissions from various growing *E. coli* cultures. Several considerations were addressed in designing the instrument. The first consideration was the need for a culturing system or a way to grow and maintain bacteria within the instrument. The next consideration was a method to capture or collect the gas emissions in a confined space. Detection of the presence of the gas and identification of the type of volatile compounds being emitted must be available. The final consideration was a means of recording the data or gas measurements automatically. Construction involved assembly of the sensor chamber and interconnections between chamber and data collection system (computer). A sensor chamber was designed to sit on a dry-block, heater, which (FIG. 2) could hold a culture vial and maintain a temperature supportive of bacterial culture growth. The chamber was rectangular in shape, approximately 10 cm in height×12.5 cm in length×10 cm in width. The chamber was constructed out of Plexiglass® and sealed to capture or contain the volatile compounds and prevent permeation of odors from the outside environment into the sensor chamber. Gas sensors, for detecting the presence of specific compounds, were mounted in the ceiling of the chamber, directly above the opening of the culture vial in the dry block heater. The gas sensors were linked to a circuit board placed on the top of the chamber, which was connected to the power source. A data acquisition module (model 232SDA12, B & B Electronics, Ottawa, Ill.) was used to convert the output from the gas sensors to digital output for recording. This module was also positioned on the chamber and directly connected to a computer housing the software for data collection. Ports for tubing were drilled into either side of the chamber; on one side the tubing was connected to a vacuum pump and the other side had tubing open to the outside. These tubes were used to evacuate and draw air through the chamber between experiments. FIGS. 1 and 1A show the overall system and FIG. 2 shows the gas sensors which are placed in the chamber ceiling. FIG. 2A shows the converter circuit.

I. Background and Significance of *Escherichia coli* O157:H7

*Escherichia coli* (*E. coli*) O157:H7 has become recognized as a significant public health concern because of its virulence as a foodborne bacterial pathogen (Buchanan and Doyle, 1997). *E. coli* O157:H7 is identified as one of the most serious foodborne pathogens due to a low infectious dose and potential severity of symptoms (Doyle et al., 1997). Though designated by O (somatic) and H (flagella) antigens, it is the specific virulence factors that separate *E. coli* O157:H7 from generic *E. coli* (Doyle et al., 1997). Current scientific research efforts and regulatory strategies emphasize obtaining a greater molecular understanding, developing effective control strategies, and enhancing detection, identification, and monitoring techniques for this organism.

The virulence factors that distinguish *E. coli* O157:H7 from generic *E. coli*, found in the gastrointestinal tract of healthy animals and humans, include specific genes encoding for the ability to attach to host cell membranes and produce specific toxins (Doyle et al., 1997). *E. coli* O157:H7 is the prominent serotype in the group referred to as Enterohemorrhagic *E. coli* (EHEC) which possess these virulence genes. *E. coli* O157:H7 is the leading cause of EHEC associated disease in the United States (Buchanan and Doyle, 1997). The pathogenesis of *E. coli* O157:H7 relies on attachment to epithelial cell walls and production of cytotoxins (Doyle et al., 1997). The attachment/effacement mechanism is due to the presence of the "eae" gene (*E. coli* attaching and effacing gene) located on the organism's chromosome. Although this gene alone does not provide virulence, it is characteristic of pathogenic EHEC strains (Buchanan and Doyle, 1997). The cytotoxins produced were identified after *E. coli* O157:H7 was determined to be a human pathogen. The toxins are referred to as verotoxin 1 and verotoxin 2, because of their toxicity to African green monkey kidney tissue cells (Vero cells), or Shiga toxin 1 and Shiga toxin 2, because the ability to produce these toxins was obtained from a bacteriophage originating from Shigella (Doyle et al., 1997). These virulence factors indicate that genetically coded differences exist between *E. coli* O157:H7 and other serotypes of *E. coli*. In developing a new technology for identifying *E. coli* O157:H7, we proposed that there could be detectable differences in the metabolic activity of *E. coli* O157:H7 due to genetic differences.

Hemorrhagic colitis is the most common human illness resulting from an *E. coli* O157:H7 infection (Buchanan and Doyle, 1997). The symptoms of hemorrhagic colitis include; mild to overtly bloody diarrhea, extremely severe abdominal cramps, and dehydration. The onset time for symptoms of hemorrhagic colitis ranges from 1–5 days following ingestion of the bacteria, with the symptomatic phase lasting 4–10 days. Systemic complications of hemorrhagic colitis patients can be life threatening. The most common sequelae is hemolytic uremic syndrome which is the leading cause of acute renal failure in children. Tarr (1995), stated that approximately 10% of younger children develop hemolytic uremic syndrome after infection with *E. coli* O157:H7. Around 15% of hemolytic uremic syndrome cases lead to chronic kidney failure and there is a 3–5% mortality rate associated with hemolytic uremic syndrome (Buchanan and Doyle, 1997). Another complication associated with *E. coli* O157:H7 infection is thrombotic thrombocytopenic purpura, which causes deterioration of the central nervous system (Boyce et al., 1995). Thrombotic thrombocytopenic purpura generally affects the elderly and is considered a more rare sequelae of *E. coli* O157:H7 infection, however the mortality rate among those afflicted is 50%. The potential severity of symptoms, particularly the mortality rate in children, necessitates research focused on enhancing food safety.

II. Epidemiology

Incidence rates for *E. coli* O157:H7 related illness were estimated to be 2.8 cases per 100,000 people in 1998. In the United States, with a population of around 272.6 million, an estimated 7,626 cases of illness due to *E. coli* O157:H7 infection occur annually (USDA-FSIS. 1998). These estimates are obtained through the Foodborne Diseases Active Surveillance Network (FoodNet) system (USDA-FSIS. 1998). Hospitalization is required in approximately 32% of *E. coli* O157:H7 infections. Surveillance for the incidence of hemolytic uremic syndrome is also conducted by FoodNet, through pediatric nephrologists. For children less than 15 years of age, the overall rate of hemolytic uremic syndrome is 8.1 cases/1,000,000 population, or approximately 2,206 cases a year in the United States (USDA-FSIS. 1998). Deaths in children, associated with hemolytic uremic syndrome, have drawn the most attention to promoting the importance of enhancing human food safety (USDA-FSIS. 1998).

The FoodNet system (USDA-FSIS. 1998) implicated undercooked ground beef as the principal food source for *E. coli* O157:H7 infections. Epidemiological links established between outbreaks of human disease and foods of bovine origin led to the identification of cattle as a reservoir for the organism (Padhye and Doyle, 1992). To enhance food safety, research efforts have expanded to focus on establishing "farm to table" control strategies. Gaining an understanding of the ecological association of *E. coli* O157:H7 with cattle and their environment and being able to identify cattle that are carriers of the organism is essential.

Cattle have been identified as asymptomatic carriers of *E. coli* O157:H7 (Cray and Moon, 1995; Garber et al., 1995). The absence of adverse health effects and lack of clinical signs in cattle make the identification of cattle carrying the organism a challenge. Generic *E. coli* is found normally in the gastrointestinal tract of ruminants, along with large populations of various other microorganisms (Brown et al., 1997). To isolate *E. coli* O157:H7 from cattle, not only does it have to be separated from the normal microflora but it must also be differentiated from other non-pathogenic serotypes of *E. coli*.

Reported prevalence rates of *E. coli* O157:H7 in bovine feces have varied across studies due to the type of cattle and production systems evaluated, the time of year, and the type of detection and culturing methods used (Buchanan and Doyle, 1997; Dargatz et al., 1997; Hancock et al., 1998; Hancock et al., 1997b). However the prevalence has been reported to be increasing over the years, primarily due to increasing sensitivity of culturing methods (Hancock et al., 1997b). Recent estimates demonstrate that *E. coli* O157:H7 is widely distributed throughout the United States (Garber et al., 1995; Hancock et al., 1997b) with 1.1–6.1% of cattle shedding the organism in their feces (Hancock et al., 1998) on approximately 75% of cattle operations (Hancock et al., 1997a; Hancock et al., 1997b). Sheep and deer have also been shown to serve as natural hosts for *E. coli* O157:H7 while remaining healthy (Buchanan and Doyle, 1997; Kudva et al., 1996; Rice et al., 1995). Companion animals have been implicated as carriers in cases of human illness as well (Trevena et al., 1996). Studies indicating that other species of animals may serve as hosts for *E. coli* O157:H7 imply that non-beef meat products can be contaminated by their pre-harvest source rather than solely by cross-contamination from beef products (Kudva et al., 1996). Food safety can be enhanced by methods to detect carriers of the pathogen and identification of pre-harvest intervention strategies.

Transmission of *E. coli* O157:H7 is typically by the fecal-oral route, and illness can result from a very low dose of less than a hundred bacteria (Buchanan and Doyle, 1997; Doyle et al., 1997). Foods of bovine origin were found to be the leading vehicle in almost 40% of *E. coli* O157:H7 outbreaks in the United States from 1982 to 1994 (Doyle et al., 1997). Other vehicles and routes of transmission include; vegetables, apple cider, cantaloupe, mayonnaise, deer jerky, drinking and recreational water, and person to person contact (Buchanan and Doyle, 1997; Doyle et al., 1997; Padhye and Doyle, 1992). Although these other vehicles exist, popular press leads us to believe that the ultimate source of contamination is contact with contaminated beef products or bovine feces. The association of *E. coli* O157:H7 with cattle and beef products has a negative impact on the beef industry, strengthening the need for research efforts in pre-harvest food safety. Research focused on developing monitoring and control strategies in meat production is important to enhance public perception of beef.

III. Current Control Strategies and Diagnostic Techniques

Food safety has become a significant focus of both the government and the scientific community, largely due to the medians attention to deaths in children associated with *E. coli* O157:H7 (Buchanan and Doyle, 1997). The Food Safety and Inspection Service of the USDA has suggested a "zero-tolerance" policy for *E. coli* O157:H7 including the testing of slaughter bound cattle. A Pathogen Reduction and Hazard Analysis Critical Control Points (HACCP) rule was published by the USDA in 1996 (Stevenson and Bernard, 1995), mandating that all USDA-inspected meat and poultry plants develop and implement HACCP plans (Stevenson and Bernard, 1995). HACCP is a systematic, preventative, process control strategy for food safety that is based on 7 principles (Stevenson and Bernard, 1995). The principles involve the identification of hazards, critical control points, critical limits, monitoring strategies, corrective actions, record keeping, and verification procedures. The potential for implementing HACCP principles "on the farm" has surfaced due to the regulations placed on packing plants and the association of *E. coli* O157:H7 with live ruminants.

HACCP Principle #4 is "Establish critical control point (CCP) monitoring requirements". In meat processing this may include monitoring the product temperature to ensure a specific internal temperature was reached or maintained. On the farm it may mean monitoring the *E. coli* O157:H7 carrier status of cattle prior to shipment for slaughter. Particularly, it would mean monitoring of prevalence of the organism following an intervention (control) strategy. Monitoring is defined as a planned sequence of observations or measurements to assess whether a previously identified CCP is under control and to produce an accurate record for future use in verification (Stevenson and Bernard, 1995). Monitoring is essential to an effective HACCP system, however the cost of detecting/monitoring a hazard can he high (Unnevhr and Jensen, 1996).

Currently, establishing the epidemiology of *E. coli* O157:H7 in live ruminants is important in efforts to identify critical control points and study the effectiveness of intervention strategies in production systems before an on-farm HACCP system can be implemented. Current techniques for determining the prevalence of *E. coli* O157:H7 in cattle usually involve the collection and culturing of feces. To identify *E. coli* O157:H7 in feces it must be selected from the normal microbial populations and be differentiated from other *E. coli* (Sanderson et al., 1995). Developing a rapid and economical technique for detecting and differentiating *E. coli* O157:H7 would greatly enhance pre-harvest food safety efforts.

Isolating *E. coli* O157:H7 from feces or food requires selective enrichment and culturing media, usually involving several steps and incubation periods. These traditional laboratory methods usually require hands-on preparation and 24–48 hours before suspect colonies can be identified. For *E. coli* O157:H7 the selectivity of the culture methods is usually based on differences in sugar fermentation (March and Ratnam, 1986; Sanderson et al., 1995; Zadik et al., 1993). Selective culturing for *E. coli* O157:H7 often includes the addition of sorbitol, rhamnose, or 4-methylumbelliferyl-$\beta$-D-glucuronide to the culture media. *E. coli* O157:H7 is unable to ferment these sugars and lacks $\beta$-glucuronidase to hydrolyze 4-methylumbelliferyl-$\beta$-D-glucuronide (Ratnam et al., 1988) (Sanderson et al., 1995). The addition of certain antibiotics not inhibitory to *E. coli* O157:H7, such as cefixime, are also used to inhibit the growth of other organisms (Sanderson et al., 1995). Following selective culturing, suspect colonies are often subjected to further testing for serotype confirmation. The biochemical, genetic, and immunologic techniques currently used have both advantages and disadvantages.

Immunoassays have been developed using selected antibodies known to react with particular antigens associated with a specific metabolite or biomass, often the toxin associated with a pathogen (Doyle et al., 1997). Latex agglutination and enzyme-linked immunosorbent assay (ELISA) are two readily available immunologic methods used for confirmation of *E. coli* O157:H7 (Doyle et al., 1997). These techniques are widely accepted, however they require that a critical mass of the metabolite or biomass exists to give a positive test result, thus requiring culturing of the organism before testing. Another disadvantage of immunoassays, based on the binding of specific antibodies to antigens, is that the organism is not isolated, so further typing is not possible (Doyle et al., 1997).

The polymerase chain reaction (PCR) method has emerged recently as a genetic technique for pathogen detection based on DNA hybridization (Doyle et al., 1997). PCR has greatly enhanced confirmation of the presence of food-borne pathogens, however it is not used routinely. Disadvantages of this technique include the inability to distinguish between live and dead bacteria, the need for pre-enrichment of samples to reduce polymerase inhibitors and other organisms, and the lack of isolation of the organism for further characterization. Genetic based assays are primarily limited to research laboratories because of the tedious and exacting nature of the reaction setup (Doyle et al., 1997).

New detection technologies can aid in the development and evaluation of intervention strategies to reduce the number of cattle carrying *E. coli* O157:H7. Several researchers have addressed potential intervention strategies that could be incorporated into production systems (Diez-Gonzalez et al., 1998; Zhao et al., 1998). The validity and efficiency of intervention strategies must be established by monitoring the presence or reduction of *E. coli* O157:H7. Rapid and economical detection methods are important for complementing these studies.

The development of a detection method that is rapid, less labor intensive, and more economically feasible would greatly enhance food safety monitoring efforts. In field research or management systems, it is not always as important to gain an understanding of the immunological or genetic properties of the organism as it is to identify the presence of the pathogen. Gas sensors can detect and identify specific compounds instantaneously and monitor them over time. Incorporated into artificial olfactory technology, gas sensors can potentially provide a convenient and inexpensive monitoring tool for certain compounds or volatile gases, such as volatile breakdown products of bacterial metabolism.

IV. Principles and Applications of Artificial Olfactory Technology

Artificial olfactory technology, referred to as an electronic nose, is finding increasing application for differentiating odors and various volatile compounds (Bartlett et al., 1997). An electronic nose is a device usually consisting of metal oxide gas sensors coupled with an artificial neural network. Analysis of compounds using this technology has been shown to be rapid, nondestructive, economical and continuous (Bartlett et al., 1997). The metal oxide sensors are based on the principle that the electrical resistance established in the sensor is decreased in the presence of specific volatile compounds. The specificity of the sensor is determined by the metal oxide used in the sensor. Sensor resistance will drop very quickly in the presence of a specific gas and recover to its original level in the absence of the gas. A simple electrical circuit can convert the change in conductivity to an output signal that corresponds to the gas concentration (Figaro USA, 1996). The output signal is reported as a voltage reading that is transferred to a computer software program for continuous plotting, generating a gas signature or pattern. An artificial neural network (ANN) is used for data analysis or pattern recognition. An ANN is an information processing system that functions similar to the way the brain and nervous system process information (Alocilja, 1998; Tuang et al., 1999). The ANN must be trained for the analysis and then tested to validate the system. In the training process, an ANN can be configured for pattern recognition, data classification, and forecasting. Commercial software programs are available for this instrument of data analysis. Recent advances with electronic nose technology have found applications in the food industry for enhancing traditional quality control techniques, based on the ability to detect rancidity, spoilage, and "off" odors (Bartlett et al., 1997).

Gardner et al. (1998) investigated the use of electronic nose technology to predict the type and growth phase of bacteria. In this study, a sensor chamber was designed that contained six metal oxide sensors chosen by their sensitivity to known products of bacterial metabolism. Two bacteria,

*Staphylococcus aureus* and *Escherichia coli*, were cultured and the headspace gas of each was monitored for 12 hours in each experimental run. The gas concentration or voltage measurements were taken every eight minutes. A back-propagation neural network was used for data analysis and prediction of bacteria type. Results showed that this technology accurately classified 100% of the *S. aureus* samples, and correctly classified 92% of *E. coli* samples. An accuracy of 81% was also seen for predicting the growth phase of the bacteria. The researchers concluded that there was considerable promise for the use of electronic nose technology to rapidly detect the type and growth phase of pathogenic organisms.

Interest in the potential of using dominant odor volatiles produced by fungi for its detection, spurred an investigation of the use of gas sensors for this purpose. Keshri et al. (1998) used an electronic nose to monitor the patterns of volatile gas production to detect activity of spoilage fungi, prior to visible growth, and differentiate between species. Six different fungi were monitored and good replication was seen among the gas patterns generated by the same species. The results indicated that early detection and differentiation of fungi species was possible using electronic nose technology to monitor the patterns of gas emissions.

The potential for field use of electronic nose technology in animal production was demonstrated in a study by Lane and Wathes (1998). An electronic nose was used to monitor the perineal odors and predict estrus in the cow. Detectable differences in the perineal odors of cows in the midluteal phase and cows in estrous were observed. However, more research was needed to find sensors more sensitive to the specific emitted volatile compounds to enhance prediction of stage in estrous. The goal of ongoing studies is to develop an electronic nose device for use in cattle operations to enhance estrus detection.

Applications of electronic nose technology for the detection of microorganisms are based on the ability to sense the volatile products resulting from metabolism (Gardner et al., 1998; Keshri et al., 1998). Current selective culturing methods for identifying *E. coli* O157:H7 are based on differences in physiological processes or biochemical reactions. Differences in sugar fermentation are seen in *E. coli* O157:H7 which are used to differentiate this serotype from other *E. coli* strains (Padhye and Doyle, 1992). The inability to ferment sorbitol and rhamnose and the lack of β-glucuronidase production are known to be indicative of *E. coli* O157:H7 (Ratnam et al., 1988; Sanderson et al., 1995; Thompson et al., 1990). These biochemical characteristics and the ability to produce specific cytotoxins indicate that genetically encoded differences could exist in the cellular physiology and metabolism between pathogenic *E. coli* O157:H7 and other strains of *E. coli*.

Enterobacteriaceae, including *E. coli*, carry out mixed acid fermentation resulting in the end product formation of ethanol, acetate, succinate, formate, molecular hydrogen, and carbon dioxide (Atlas, 1995). In this study, it was hypothesized that an electronic nose could be used to detect the volatile compounds produced by various *E. coli* strains and differentiate serotype O157:H7 based on a unique pattern of gas emissions. An instrument was designed that contained biosensors sensitive to known end products of microbial metabolism: ammonia and nitrogenous compounds; methane, ethanol, and isobutane; and hydrogen sulfide (Atlas, 1995; Gardner et al., 1998; Moat and Foster, 1995). Selecting several sensors reactive co various compounds was important for later studies involving other types of bacteria. Based on the detectable differences observed between the gas patterns of generic *E. coli* and *E. coli* O157:H7 and further evaluation of gas sensors it may be possible to identify a single gas sensor capable of demonstrating metabolic differences between strains of bacteria (Younts et al., 1999).

Conclusion

In the midst of current efforts to reduce human exposure to foodborne pathogens, animal production has come under scrutiny as a potential source of these organisms. The government, scientific community, and producers are aware of a need to study the epidemiology and control of pathogens "on the farm". Electronic nose technology has the potential to enhance efforts addressing pre-harvest food safety concerns involving *E. coli* O157:H7, by providing a convenient, economically feasible, and less labor intensive tool for identifying carrier cattle or other environmental sources/reservoirs of the organism. Advantages of an electronic nose as a diagnostic tool would include the identification of live bacteria and monitoring of their growth, no requirement for reagents, and the capability of being automated.

Rapid and economical detection of human pathogens in animal and food production systems would enhance food safety efforts. The objective of this research was to develop a gas sensor based instrument, coupled with an artificial neural network (ANN), which is capable of differentiating the human pathogen *E. coli* O157:H7 from non-O157:H7 *E. coli* isolates. The production of gases from eight laboratory isolates and 20 field isolates of *E. coli* were monitored during growth in laboratory conditions, and a unique gas signature for each isolate was generated. An ANN was used to analyze the gas signatures, and classify the bacteria as O157:H7 or non-O157:H7 *E. coli*. Detectable differences were observed between the gas signatures of the *E. coli* O157:H7 and non-O157:H7 isolates and the ANN classified the isolates with a high degree of accuracy. Based on this work, gas sensor based technology has promise as a diagnostic tool for pathogen detection in pre-harvest and post-harvest food safety.

Metal oxide gas sensors were acquired from a proprietary vendor (Figaro USA, Inc., Glenview, Ill.) to detect, measure, and monitor the volatile gases released from the bacterial cultures. The following description of the sensor operating principle was obtained from the "General Information for TGS Sensors" (Figaro USA, 1996). In these sensors, a chemical reaction occurs between the metal oxide, usually $SnO_2$, in the sensor and the volatile gas it is designed to detect. An electrical current flows between connected micro crystals of metal oxide within the sensor. The sensing material, metal oxide, has a negative charge on the surface and absorbs oxygen, which accepts electrons, leading to a positive charge. The resulting surface potential can act as a potential barrier against electron transfer, increasing the electrical resistance within the sensor. The volatile compound for which the sensor is specifically designed to detect serves as a reducing gas. When this compound is present, the negatively charged oxygen density on the surface between the metal oxide crystals is decreased. The height of the barrier against electron transfer is reduced and there is a decrease in sensor resistance. The amount of decrease in sensor resistance is proportional to gas concentration; the higher the gas concentration the greater the increase in electron flow. The decrease in sensor resistance, or increase in electrical conductivity, is converted to a change in voltage by the circuit board. The voltage readings are fed to the data acquisition board and transferred to the computer for continuous plotting.

The sensors employed in our instrument were chosen based on their ability to detect volatile metabolites known to be produced from bacterial metabolism (Moat and Foster, 1995). Four gas sensors were used, specific for the following: amines (sensitivity of 30 ppm ammonia in air, Figaro TGS 826), alcohol (50–5,000 ppm, Figaro TGS 822), air contaminants (1–10 ppm, Figaro TGS 800), and hydrogen sulfide (5 ppm, Figaro TGS 825). The amine sensor is very sensitive to ammonia and amine compounds; the alcohol sensor to methane, iso-butane, and ethanol; and the air contaminants sensor to similar alcohol compounds at lower concentration (Figaro USA, 1996). Two additional sensors were used to monitor the ambient temperature (Figaro D Thermistor) and relative humidity (Figaro NHU-3) within the instrument. Monitoring the stability of temperature and humidity is critical due to their effects on the sensitivity of the sensors. A change in temperature or relative humidity can affect the rate of the chemical reaction as it occurs within each sensor (Figaro USA, 1996).

A data acquisition software program (MeterBOSS, Teramar Group, Inc., El Paso, Tex.), was used to collect and record each sensor response. This program controlled the rate of gas sampling and plotted the voltage readings generating a pattern or gas signature during the length of each experimental run. The gas patterns could then be analyzed for differences and similarities for classification of the bacterial strains.

Artificial Neural Network Selection for Data Analysis

An artificial neural network (ANN) was chosen for the analysis and interpretation of the gas signatures. An ANN is an information processing system that is patterned after the way the brain and nervous system process information (Alocilja, 1998; Tuang et al., 1999). For this investigation, we employed a back-propagation neural network (BPN) algorithm (BrainMaker, California Scientific Software, 1998). The standardized data from each experiment, the gas signature data points, serves as the input vector. The desired output vector is the classification of the organism, "0" for non-O157:H7 E. coli and "1" for E. coli O157:H7. Training is accomplished by using a standardized data set (standard gas signatures) and associating the input or gas signature with the desired output or classification. The program compares the data and computes network output with the desired output until an acceptable level of recognition is achieved. Another set of data is used for testing the predictive capability of the trained BPN. In testing, the BPN is exposed to the input vectors not labeled with the bacteria type or desired output classification. Evaluation of the training is based on the ability of the BPN to recognize and accurately classify the bacteria type from the input gas signature. The efficacy of the sensing instrument for differentiating E. coli O157:H7 from non-O157:H7 isolates is determined by the ability of the BPN to distinguish between gas signatures and correctly classify the bacteria type.

Bacteria Isolates and Culturing

Characterized strains of E. coli, four isolates of E. coli O157:H7 and four non-O157:H7 serotypes, from various sources were obtained for use in the investigation (Table 1. Two of the isolates were obtained from Michigan State University and the remaining six isolates were

TABLE 1

Serotypes and sources of E. coli isolates

| Isolate | Serotype | Source |
| --- | --- | --- |
| Lab Non-O157:H7 | Non-O157:H7 | Veterinary Medical Center, Michigan State University |
| E47411/0 | O5:H- | Dr. Qijing Zhang The Ohio State University |
| 80-2572 | O157:H13 | Dr. Qijing Zhang The Ohio State University |
| SD89-3143 | O111:NM | Dr. Qijing Zhang The Ohio State University |
| Lab O157:H7 | O157:H7 | Veterinary Medical Center, Michigan State University |
| ATCC 43895 | O157:H7 | Dr. Qijing Zhang The Ohio State University |
| CDC B8038-MS1/0 | O157:H7 | Dr. Qijing Zhang The Ohio State University |
| E29962 | O157:H7 | Dr. Qijing Zhang The Ohio State University | obtained from The Ohio State University. These isolates were independently verified as E. coli O157:H7 or non-O157:H7 E. coli by the Bacteriology Laboratory at the Veterinary Diagnostic Center, University of Nebraska, Lincoln, Neb. For verification as E. coli O157:H7, the isolates were subject to PCR for the presence of the eae gene, Shiga toxin (STX) structural gene and the O antigen biosynthesis (rfb) loci. All experiments were performed in a certified Biological Safety Level II laboratory.

Media Testing

Two types of bacterial culture media, Brain Heart Infusion Broth (BHI) and Nutrient Broth (Difco Laboratories, Detroit, Mich.), were evaluated for their use in the investigation. Two isolates of E. coli, one O157:H7 serotype and one non-O157-H7 serotype, were used for the comparison. Both isolates were grown individually in each media. For each experiment, 10 ml of the media was placed in a sterile 14 ml polystyrene vial then inoculated with 100 colony forming units (CFUs) of one of the isolates. The vial was centrally placed in the dry block heater, maintained at 37±0.2° C., and monitored over time within the sensor chamber. The gas readings were collected at a one minute sampling rate, plotted over 20 hours and a gas signature generated for each experiment.

Bacteria Concentration Testing

To determine if there were differences in the gas signatures based on the presence of different concentrations of the same bacteria, a study was conducted using different initial concentrations of bacteria. The concentrations of the bacteria stock cultures were determined by serial dilution and viable plate counts. Bacterial concentrations of $10^2$, $10^3$, $10^4$, $10^5$, $10^6$, and $10^7$ per ml, were used for the initial inoculum and monitored over time to determine the occurrence of the initial voltage increase. For each experiment, the desired concentration of bacteria was introduced into 10 ml of nutrient broth and the vial was centrally placed in the dry block heater, maintained at 37±0.2° C., within the sensor chamber. Both E. coli O157:H7 and non-O157:H7 E. coli isolates were assayed at the different inoculum concentrations to determine the time each concentration required to reach the initial voltage increase. Gas patterns or signatures were identified starting at the initial voltage increase and ending when the voltage readings decreased to levels equivalent or less than those prior to the initial increase.

Control Testing

The dry block heater and uninoculated media were monitored over time to determine if detectable volatile compounds, not associated with bacterial growth, were being released. The sensor chamber was placed over the dry block heater with nothing in it. The sensor readings were taken at a one minute sampling rate for 20 hours. For monitoring the volatile compounds from the media, 10 ml of nutrient broth was placed in a sterile 14 ml polystyrene vial. The vial was placed in the dry block heater at 37±0.2° C. with the sensor chamber in place and monitored at a one minute sampling rate for twenty hours.

Growth Curves

The growth activity of the microorganisms in nutrient broth within the gas sensor instrument was monitored to investigate the relationship between bacterial growth and gas emissions. All eight isolates of *E. coli* were used in this experiment. Cultures were grown and maintained in nutrient broth to establish a stock culture of each isolate. There were two separate experimental runs on each isolate, making a set of 16 growth curves. For each isolate, a predetermined concentration of $10^5$ CFUs/ml, was introduced to a sterile polystyrene vial containing 10 ml of nutrient broth. The vial was then placed in the dry block heater within the sensor chamber. At 2-hour intervals the sensor chamber was lifted and 100 μl of the sample culture was drawn out of the vial using a pipette over a 16 hour period. The 100 μl samples were serially diluted and viable plate counts were performed. The results from the plate counts were plotted over the 16 hour time period to establish standard growth curves for each isolate.

Results

Media Testing

Figure 3:
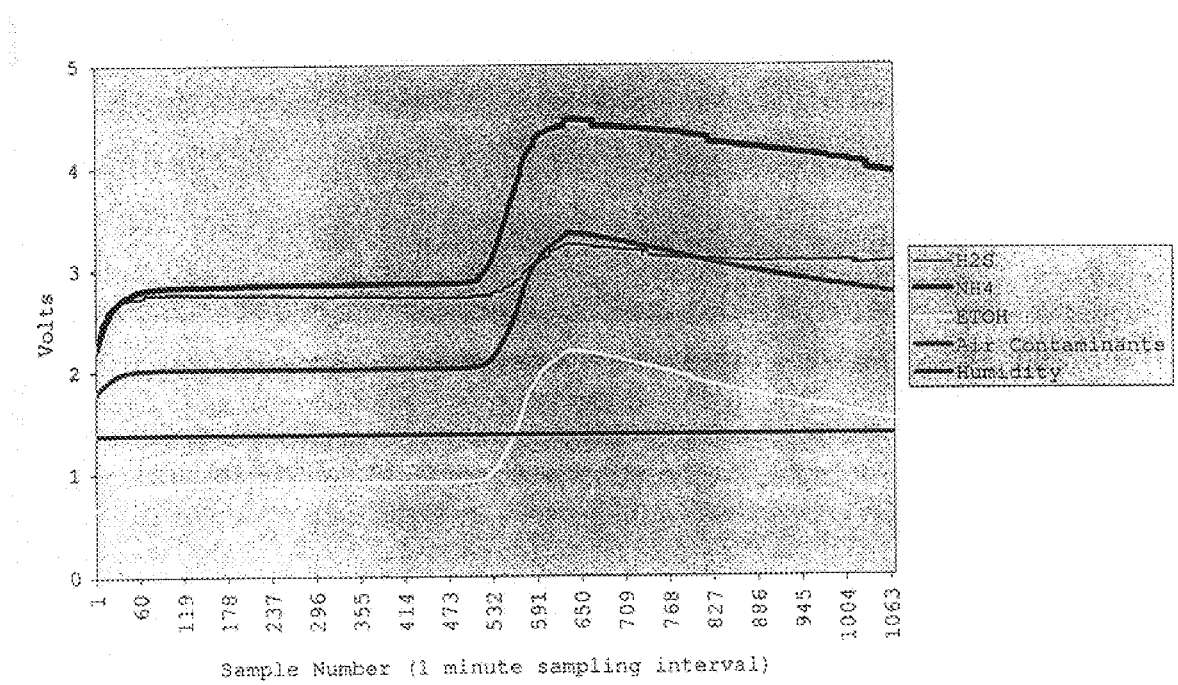
FIG. 3 is a graph of a representative gas signature generated by non-O157:H7 E. coli in BHI broth.
Figure 4:
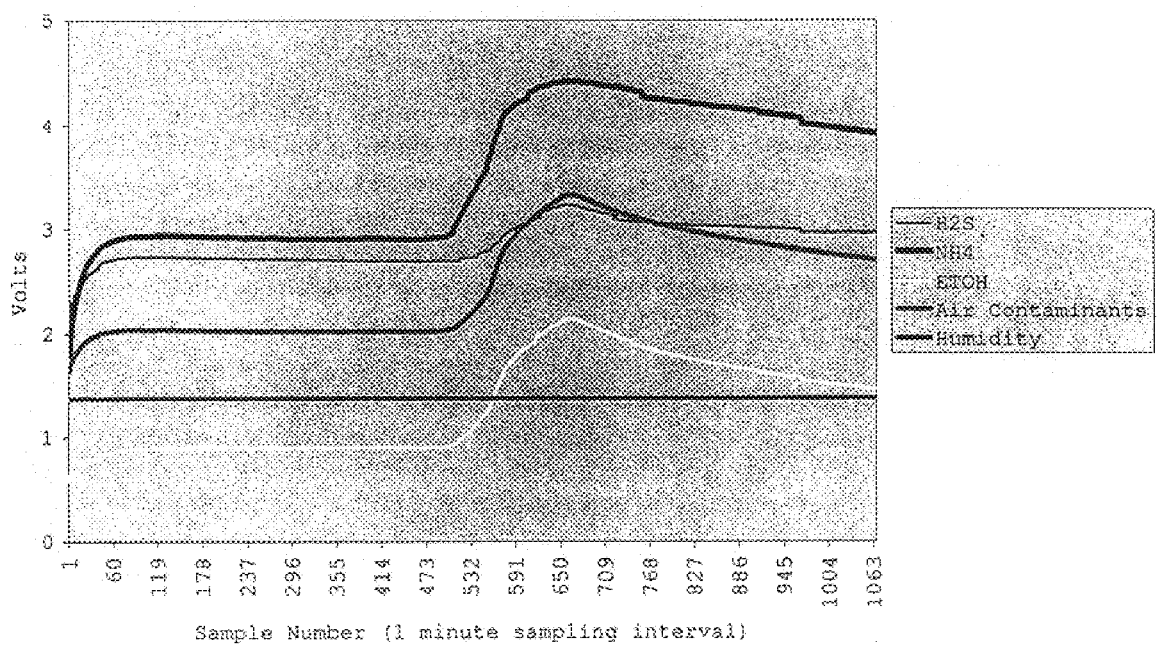
FIG. 4 is a graph of a representative gas signature generated by E. coli O157:H7 in BHI broth.
Figure 5:
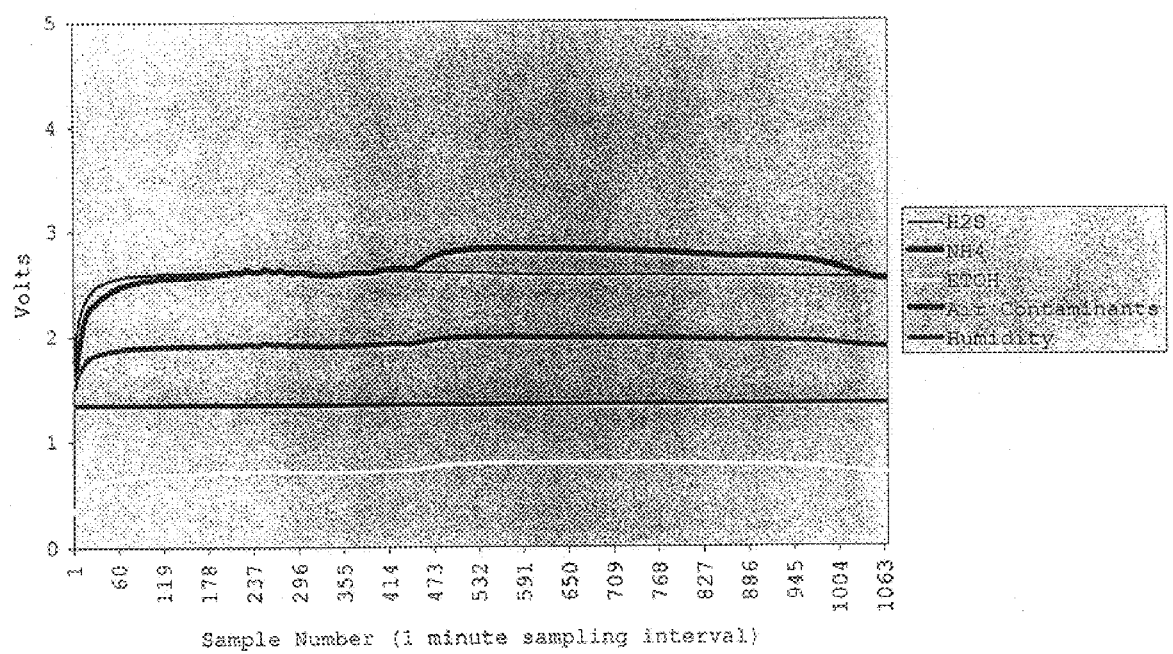
FIG. 5 is a graph of a representative gas signature generated by E. coli O157:H7 in nutrient broth.
Figure 6:
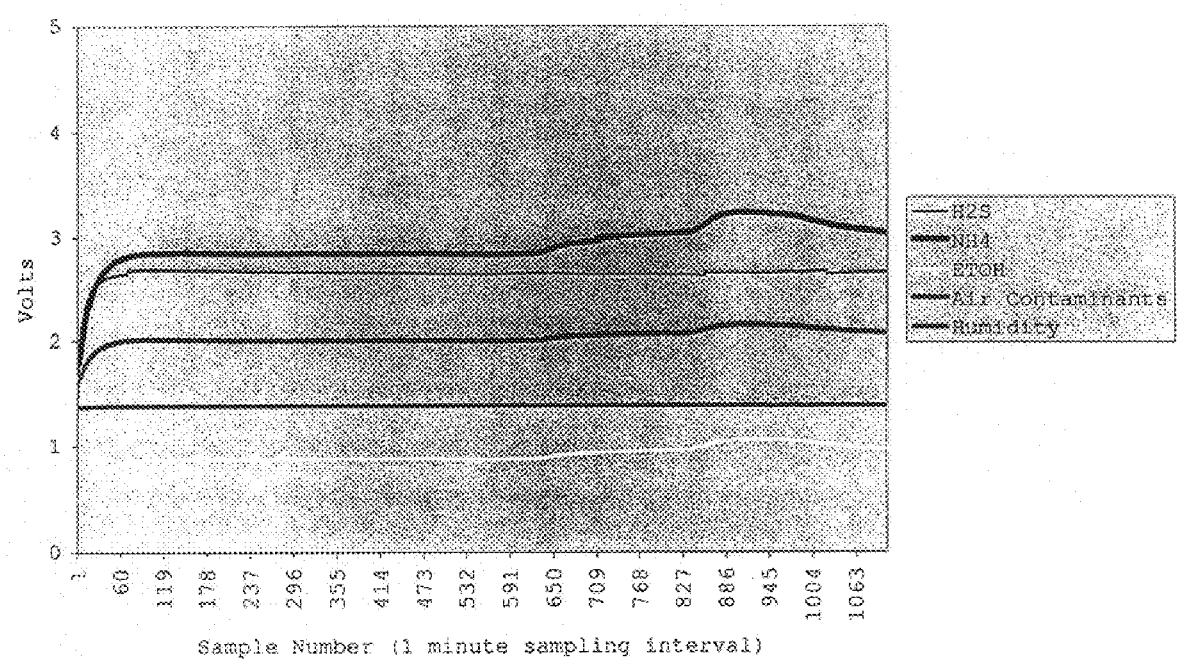
FIG. 6 is a graph of a representative gas signature generated by non-O157:H7 E. coli in nutrient broth.

The results of the experiments in BHI media demonstrated that gas emissions could be detected from the growing cultures. A distinct increase in voltage readings was seen over time for each of the gas sensors. In the BHI broth, the voltage readings dramatically increased initially, peaked, then tapered off. No obvious differences were observed between the gas emissions from the O157:H7 and the non-O157:H7 isolates. FIGS. 4 and 3 show representative gas signatures for *E. coli* O157:H7 and non-O157:H7 *E. coli* in BHI. Visually detectable differences were observed between the gas signatures of the *E. coli* O157:H7 isolate and the non-O157:H7 isolate when grown in nutrient broth. The initial increase in voltage in the nutrient broth was not as dramatic as observed in the BHI media. The gas pattern observed for the *E. coli* O157:H7 isolate grown in nutrient broth showed an initial increase and a period of stabilization followed by a gradual decrease in the voltage readings (FIG. 5). A binary increase in voltage was observed with the non-O157:H7 *E. coli* isolate followed again by a period of tapering off (FIG. 6). Excellent reproducibility was seen in the pattern of gas emissions between the replicate experiments for each isolate. Based on these observations, we decided to employ nutrient broth as the growth media for further investigation of the instrument.

Bacteria Concentration Testing

Figure 7:
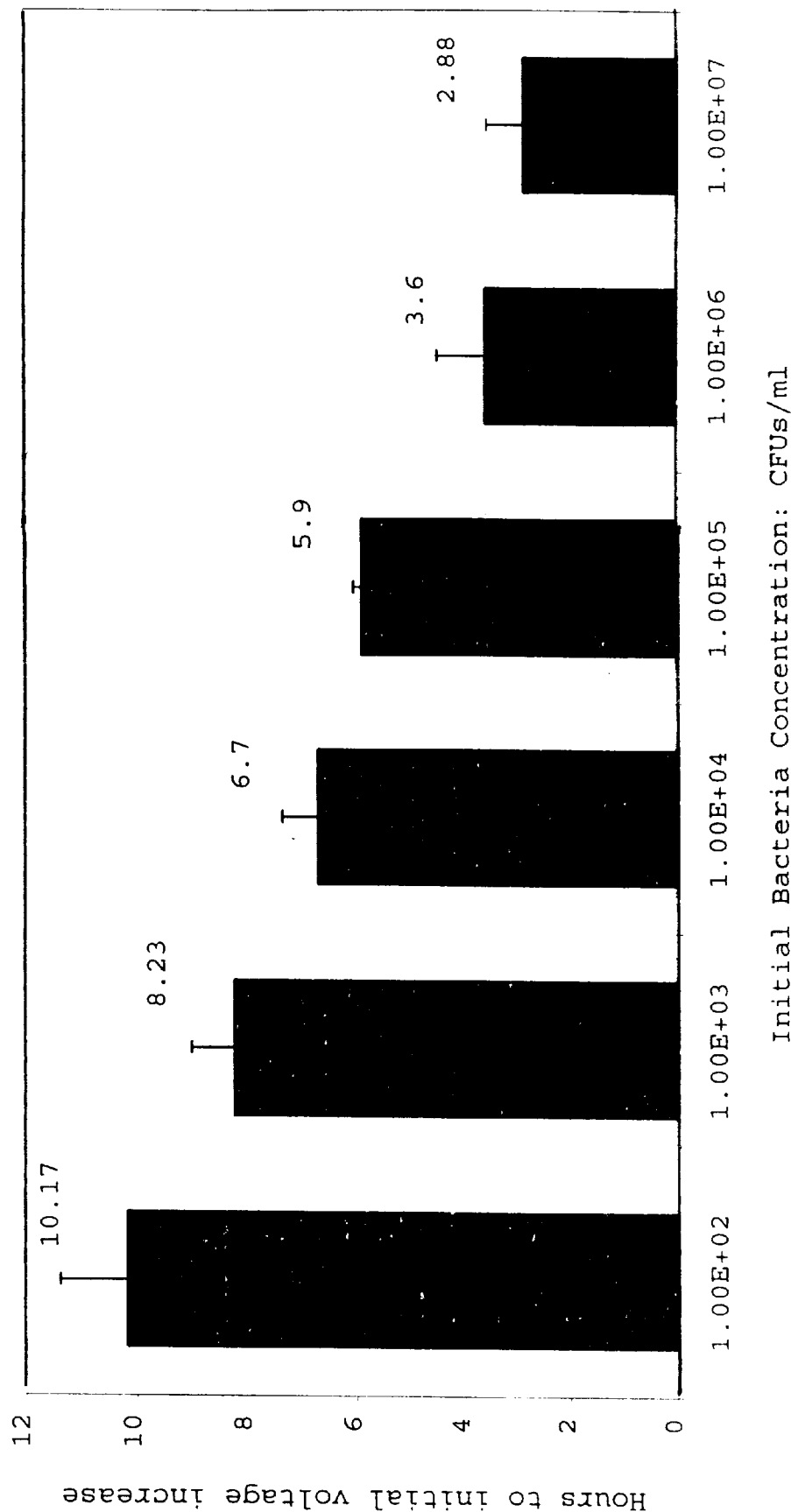
FIG. 7 is a graph showing an average time in hours (+/− standard deviation) for initial increase in gas concentration to occur, as measured by voltage increase in gas sensors, at different initial bacteria concentrations.

The presence of a detectable level of gas concentration was reached sooner with a higher initial concentration of bacteria. The gas patterns for the same bacteria were similar in shape over the different concentrations. However, the initial voltage change occurred later for each decrease in initial bacteria concentration. FIG. 7 shows the initial bacteria concentration and the average time in hours required for the initial voltage increase to be observed. To establish repeatable standard gas signatures for *E. coli* O157:H7 and non-O157:H7 *E. coli* isolates a standard initial concentration of $10^5$ colony forming units (CFU's) per ml and a monitoring time of 16 hours was used for further experiments. A concentration of $10^5$ CFU's/ml was chosen because it optimized the length of time in which a consistent gas signature could be obtained.

Control Testing

Figure 8:
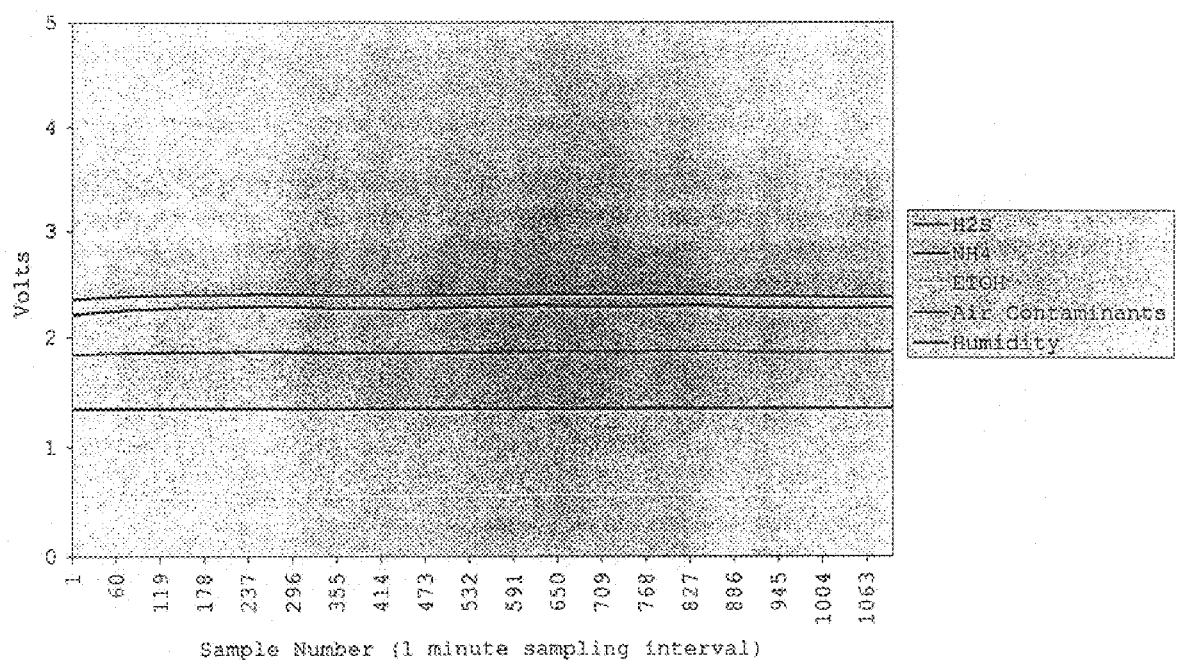
FIG. 8 is a graph of a control gas signature from monitoring dry block heater.
Figure 9:
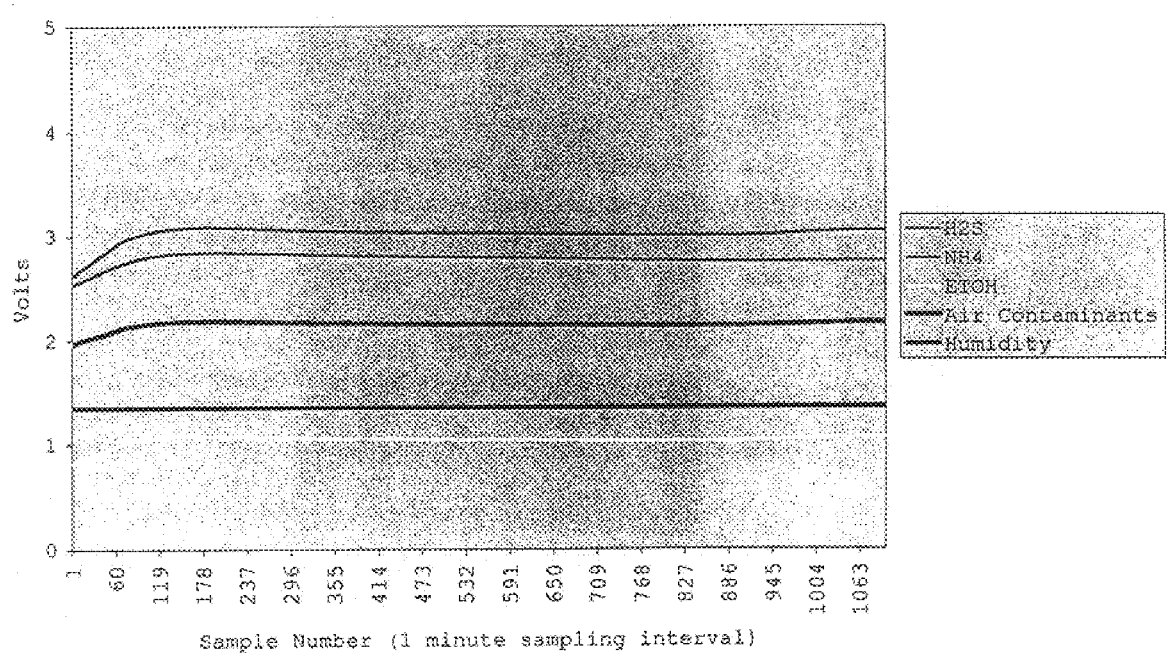
FIG. 9 is a graph of control gas signature from monitoring nutrient broth.

No voltage change was observed when the dry block heater was monitored for release of volatile compounds over time (FIG. 8). Monitoring of uninoculated nutrient broth initially showed a slight increase in voltage over time (FIG. 9). This increase was expected as the media was warmed to 37° in the heater and volatile compounds could be detected. The decrease in sensor resistance was even and eventually stabilized indicating that volatiles from the media did not impact the gas signatures seen with the bacteria cultures.

Growth Curves

Figure 10:
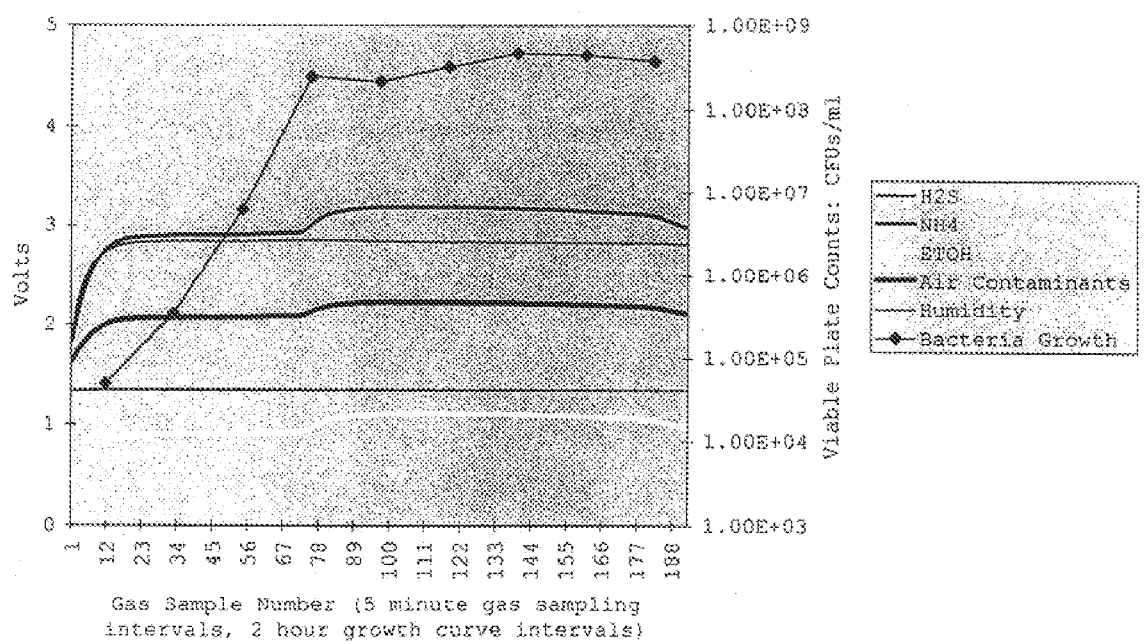
FIG. 10 is a graph of a representative growth curve for E. coli O157:H7 plotted against a typical gas signature.
Figure 11:
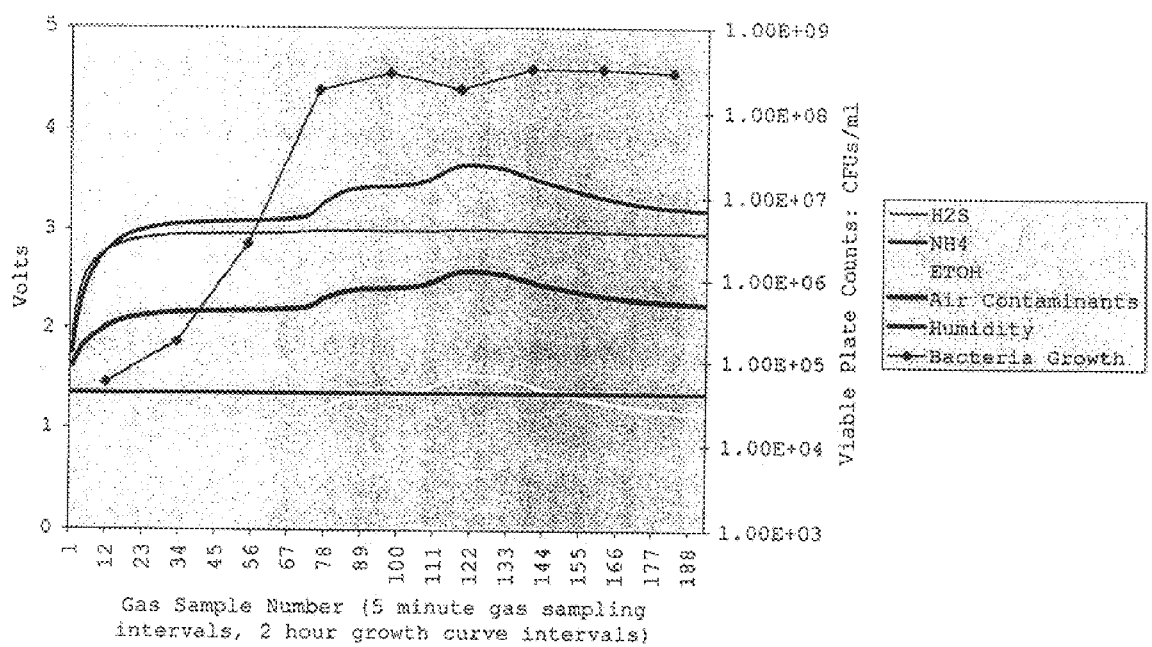
FIG. 11 is a graph of a representative growth curve for non-O157:H7 E. coli plotted against a typical gas signature.

Representative growth curves plotted against gas signatures for *E. coli* O157:H7 and for non-O157:H7 *E. coli* are shown in FIGS. 10 and 11 respectively. The figures demonstrate the relationship between the lag, log, and stationary phases of microbial growth and the occurrence of gas emissions within the sensing system. It was repeatedly observed that the initial voltage change or detection of gases occurred during the mid to late log phase of bacterial growth. It was also observed that the voltage stabilized during the stationary growth phase.

Control Testing

No voltage change was observed when the dry block heater was monitored for release of volatile compounds over time (FIG. 8). Monitoring of uninoculated nutrient broth initially showed a slight increase in voltage over time (FIG. 9). This increase was expected as the media was warmed to 37° in the heater and volatile compounds could be detected. The decrease in sensor resistance was even and eventually stabilized indicating that volatiles from the media did not impact the gas signatures seen with the bacteria cultures.

Growth Curves

Representative growth curves plotted against gas signatures for *E. coli* O157:H7 and for non-O157:H7 *E. coli* are shown in FIGS. 10 and 11 respectively. The figures demonstrate the relationship between the lag, log, and stationary phases of microbial growth and the occurrence of gas emissions within the sensing system. It was repeatedly observed that the initial voltage change or detection of gases occurred during the mid to late log phase of bacterial growth. It was also observed that the voltage stabilized during the stationary growth phase.

Discussion

A gas sensor based instrument was developed for use in investigating the potential of identifying *E. coli* O157:H7 based on the pattern of volatile gases released during growth. The instrument was capable of detecting the gas emissions from growing *E. coli* cultures. Differences in the gas patterns were seen based on the media and bacteria concentration employed. The variations in gas patterns based on the type of media used are most likely due to differences in the nutrient composition of the media that resulted in different metabolic breakdown products. No obvious visual differences in the gas patterns produced by *E. coli* O157:H7 and non-O157:H7 isolates were observed when cultured in BHI broth. However, recognizable differences were observed in the gas patterns when cultured in nutrient broth. This suggests that some component of nutrient broth is metabolized differently by the two types of bacteria, resulting in different patterns of gas production. The amount of time that it took to first detect gas production was dependent on the initial bacterial concentration introduced into the test system. Initial detection of gas occurred faster when a higher concentration of bacteria was used.

This suggests that a critical mass of bacteria must be present to produce detectable levels of the gases. Control testing established that the media and sensor apparatus do not give off volatile gases which may be interpreted as bacterial gas production.

Preliminary observations allowed for the defining of appropriate protocols for standard experiments to be used in investigating the use of the electronic nose for differentiating *E. coli* O157:H7 from non-O157:H7 *E. coli*. Based on these results, standard experiment protocols were developed to include: using nutrient broth as the growth medium, starting with an initial bacteria concentration of $10^5$ CFUs/ml, monitoring the gas emissions for a period of 16 hours, and analyzing the gas signatures using an ANN trained with standardized data sets.

EXAMPLE 2

Differentition of *Escherichia Coli* O157:H7 from Non-O157:H7 *E. Coli* Serotypes Using a Gas Sensor Based, Computer-Controlled Detection System Introduction A great deal of media and regulatory attention has been focused on *E. coli* O157:H7 because of potential human pathogenicity and association with ground beef and other commonly consumed foods (Buchanan and Doyle, 1997). Human illness associated with the consumption of contaminated beef has led to the identification of cattle as a reservoir for *E. coli* O157:H7 (Buchanan and Doyle, 1997; Padhye and Doyle, 1992). Detecting and controlling pathogenic *E. coli* in beef production management is being proposed, yet little is currently known about "on the farm" environments affecting the presence, magnitude, and duration of this organism (Brown et al., 1997). *E. coli* are part of the natural intestinal flora of cattle (Padhye and Doyle, 1992). Rapid differentiation of pathogenic *E. coli* is essential for determining prevalence and monitoring the efficacy of intervention strategies in farm and processing environments. Currently, detection and differentiation techniques are often time consuming, expensive, and lack sensitivity. Developing a rapid and economical technique for detecting and differentiating *E. coli* O157:H7 would greatly enhance pre-harvest food safety efforts.

Artificial olfactory technology, referred to as an "electronic nose", is finding increasing application for differentiating odors and various volatile compounds (Gardner et al., 1998; Keshri et al., 1998; Lane and Wathes, 1998). An electronic nose is a device usually consisting of metal oxide gas sensors coupled with an artificial neural network (ANN). The gas sensors detect volatile compounds and generate a gas signature, which is interpreted by the ANN. Recent advances with this instrumentation have found application in the food industry for detecting rancidity, spoilage, and "off" odors (Bartlett et al., 1997). The use of an electronic nose shows promise for monitoring the odor quality of food products throughout the food chain. This technology has also been studied for its application in differentiating various types of bacteria. Gardner et al. (1998) showed that an electronic nose could differentiate between *Staphylococcus areus* and generic *E. coli* with almost 100% accuracy. Detection and differentiation of species of fungi in early phases of growth has also been successful (Keshri et al., 1998).

A gas sensor based instrument could provide an economically viable, easy-to-use tool for identifying possible sources of contamination in cattle production before infection spreads and enters the food supply. The objective of this investigation was to evaluate a sensor based instrument for detecting and differentiating *E. coli* O157:H7 from non-O157:H7 isolates through gas emissions in laboratory cultures. The long term objective of this research is to develop a diagnostic tool for identifying *E. coli* O157:H7, thus enhancing pre-harvest food safety efforts.

Materials and Methods

Instrumentation

A sensor chamber was built containing an array of 4 metal oxide gas sensors (Figaro USA, Inc., Glenview, Ill.), a temperature sensor, and a humidity sensor. The metal oxide gas sensors were chosen based on their capability to detect common volatile breakdown products of bacterial metabolism (Moat and Foster, 1995). Table 2 shows the sensor type, target compounds it detects, and sensitivity. The sensor detects the specific volatile compound which causes electrical conductivity within the sensor to

TABLE 2

Sensors employed in instrument with detectable compound specificity and sensitivity levels

| Gas Sensors | Specific Compounds | Sensitivity |
| --- | --- | --- |
| TGS 826 Ammonia | Ammonia, amines | 30 ppm |
| TGS 822 Alcohol | Methane, iso-butane, ethanol | 50–5000 ppm |
| TGS 800 Air Contaminants | Methane, iso-butane, ethanol | 1–10 ppm |
| TGS 825 Hydrogen Sulfide | Hydrogen Sulfide | 5 ppm | increase. The electrical signals generated by this increased conductivity are acquired by a data acquisition board, connected to a computer. A computer software program (MeterBOSS, Teramar Group, Inc., El Paso, Tex.), was used to record and continuously plot the voltage readings, generating the gas signatures.

Culturing and Collection of Gas Emissions

Characterized strains of *E. coli*, four isolates of *E. coli* O157:H7 and four non-O157:H7 serotypes, from various sources were obtained for testing (Table 3). The isolates were verified as being *E. coli* O157:H7 by the Bacteriology Laboratory at the Veterinary Diagnostic Center, University of Nebraska, Lincoln, Neb. The isolates were grown and maintained in multipurpose nutrient broth (Difco Laboratories, Detroit, Mich.). All culturing was performed in a certified Biological Safety Level II

TABLE 2

Serotypes and sources of *E. coli* isolates

| Isolate | Serotype | Source |
| --- | --- | --- |
| Lab Non-O157:H7 | Non-O157:H7 | Veterinary Medical Center, Michigan State University |
| E47411/0 | O5:H- | Dr. Qijing Zhang The Ohio State University |
| 80-2572 | O157:H13 | Dr. Qijing Zhang The Ohio State University |
| SD89-3143 | O111:NM | Dr. Qijing Zhang The Ohio State University |
| Lab O157:H7 | O157:H7 | Veterinary Medical Center, Michigan State University |
| ATCC 43895 | O157:H7 | Dr. Qijing Zhang The Ohio State University |
| CDC B8038-MS1/0 | O157:H7 | Dr. Qijing Zhang The Ohio State University |

TABLE 2-continued

Serotypes and sources of *E. coli* isolates

| Isolate | Serotype | Source |
| --- | --- | --- |
| E29962 | O157:H7 | Dr. Qijing Zhang The Ohio State University | laboratory. Based on previous studies (Younts, 1999), four standardized experimental runs were performed on each isolate making a total set of 32 experimental runs or gas signatures. First, 10 ml of nutrient broth was placed into a sterile 14 ml polystyrene vial. A set concentration of bacteria, $10^5$ colony forming units (CFU) per ml (Younts et al., 1999), was introduced into the vial from culture stocks. The vial was centrally placed in a 37±0.2° C. dry block heater and grown within the sensor chamber. Each experiment ran for 16 hours with gas sampling every five minutes. The gas readings or voltage measurements were continuously plotted, generating a gas signature. Preliminary studies identified the initial cell concentration and time interval most appropriate for experimental standardization (Younts et al., 1999).

Pattern Interpretation by the Artificial Neural Network

Each of the four experimental runs on every *E. coli* isolate generated a standardized gas signature for that isolate, providing four gas signatures for each isolate. Data set "1" consisted of the signatures from the first experimental run on each isolate. Data sets "2", "3", and "4" were made up of the gas signatures from each subsequent experimental run. The data were divided equally into training and testing sets for the neural network analysis. In the training process the ANN was configured for data classification. The data sets were used in different combinations as part of the training and testing of the ANN. For example, data sets 1 and 2 were used as the training set and sets 3 and 4 were used as the testing set for one train-test scenario. The next scenario used data sets 3 and 4 for training and 1 and 2 for testing. The third scenario involved data sets 1 and 3 for training and sets 2 and 4 for testing. There were a total of six scenarios for each responding sensor type (Table 4). The recognition/classification by the ANN is based on the shape of the gas pattern, not specific time-data points. Although

TABLE 4

Scenarios for training and testing the ANN

| Scenario | Training Set | Testing Set |
| --- | --- | --- |
| 1 | 1 & 2 | 3 & 4 |
| 2 | 3 & 4 | 1 & 2 |
| 3 | 1 & 3 | 2 & 4 |
| 4 | 2 & 4 | 1 & 3 |
| 5 | 1 & 4 | 2 & 3 |
| 6 | 2 & 3 | 1 & 4 | the shapes of the gas signatures are similar there is fluctuation in the voltage readings at specific times due to difference in gas concentration intensity. This fluctuation in voltage level affects the ability of the ANN to recognize unseen patterns and accurately classify them. By dividing the data into testing and training sets, the specific patterns used to "test" the ANN analysis have not been seen before. The ANN is programmed to recognize a gas pattern shape based on the training set. When tested, the ANN calculates the probability that the previously unseen patterns in the testing set are indicative of a desired classification. For example, the ANN compares each gas signature in the testing set with the patterns it was "trained" to recognize from the training set. The resulting output from the ANN is the probability for each testing pattern, or isolate gas signature, that it is *E. coli* O157:H7 or non-O157:H7 *E. coli*. For each training and testing scenario the previous training/testing scenario was deleted and the ANN was re-trained and tested. The sensitivity and specificity of detecting *E. coli* O157:H7 for each scenario was calculated and then averaged together.

Test Accuracy

The sensing system was evaluated for its value as a screening test for *E. coli* O157:H7. Based on the differences in the gas patterns of the two *E. coli* groups, O157:H7 and non-O157:H7, the ANN generated probabilities that individual gas signatures were representative of *E. coli* O157:H7 or not. Based on the correctness of the classification from the probabilities, the sensitivity and specificity of the instrument were calculated (Smith, 1995).

Results

Gas Signatures

Figure 12:
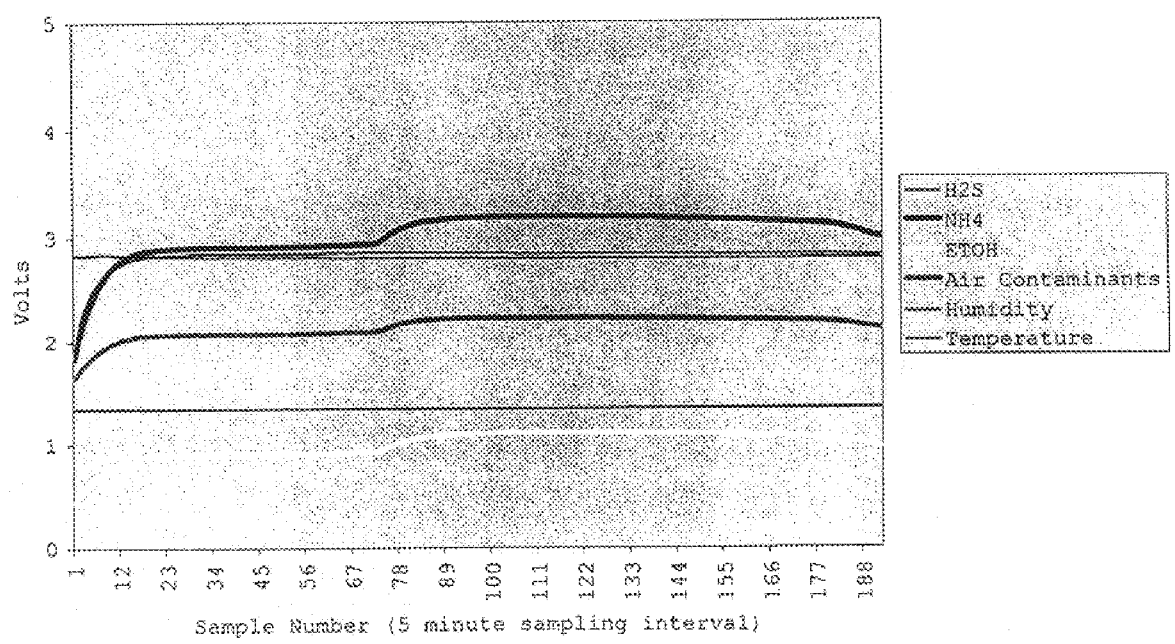
FIG. 12 is a graph of a representative gas signature generated by E. coli O157:H7.
Figure 13:
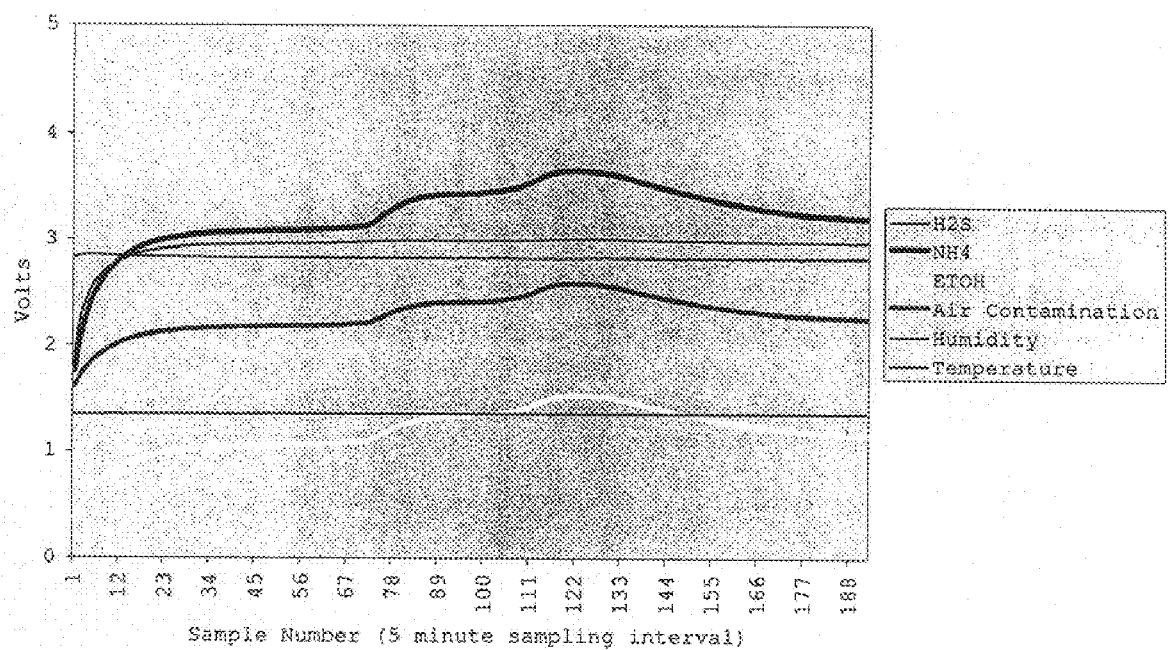
FIG. 13 is a graph of representative gas signature generated by non-O157:H7 E. coli.

Detectable differences were observed between the gas signatures of the *E. coli* O157:H7 and the non-O157:H7 isolates. The gas pattern observed for the *E. coli* O157:H7 showed an initial increase and a period of stabilization followed by a gradual decrease in the voltage readings (FIG. 12). A binary increase in voltage was observed with the non-O157:H7 *E. coli* isolate followed again by a period of tapering off (FIG. 13). Subjectively, there was reliable reproducibility observed between the gas patterns of replicate experiments on each isolate and within the two groups. The same overall signature shape was seen for the *E. coli* O157:H7 isolates. There was greater variation in the shape of the gas patterns from the non-O157:H7 isolates. Although four sensors were used in monitoring gas production, only the ammonia, air contaminant, and alcohol sensors showed a response over time. No gas pattern resulted from the hydrogen sulfide sensor, as was anticipated because hydrogen sulfide is not a normal byproduct of *E. coli* metabolism. The temperature and humidity measurements remained consistent over time.

Artificial Neural Network Analysis

The outputs of the three sensors (ammonia, air contaminant, and alcohol) were used to train and test the neural network for classifying *E. coli* O157:H7. Based on the evaluation of test accuracy (Smith, 1995), the ANN had high predictive capability for accurately classifying the bacteria based on the output of individual sensors. The results of the sensitivity and specificity analysis for the three sensors and scenarios are presented in Tables 8, 6 and 7. Sensitivity and specificity varied depending on the probability cut off used to classify the gas signatures as O157:H7 and non-O157:H7 *E. coli*. As an example, for the first cut off point any signature with a 50% or greater probability of being *E. coli* O157:H7 was considered "positive". For all sensors, as the probability cut off point was reduced, the ability to correctly classify *E. coli* O157:H7 increased while the rate of misclassification of non-O157:H7 *E. coli* also increased.

Discussion

An analytical instrument has been developed capable of detecting and differentiating *E. coli* O157:H7 from non-O157:H7 *E. coli* isolates in a laboratory setting. Gas-specific sensors were used to detect volatile compounds produced by bacteria during normal metabolic activity. The gas patterns generated are most likely due to the presence of amines, nitrogenous compounds, and alcohols, which are common metabolic breakdown products known to be associated with *E. coli* (Moat and Foster, 1995). The hydrogen sulfide sensor did not show a response over time due to the fact that hydrogen sulfide is not a normal by-product of *E. coli* metabolism (Moat and Foster, 1995). However, inclusion of

TABLE 5

Sensitivity and specificity of the gas sensor instrument based on the artificial neural network interpretation of the ammonia sensor output

| Interpretation by the ANN | Ammonia Sensor | | | |
|---|---|---|---|---|
| Probability of EC O157:H7 Considered Positive | Mean Sensitivity (%) | Sensitivity Range (%) | Mean Specificity (%) | Specificity Range (%) |
| 50% | 91.7 | 75–100 | 70.83 | 37.5–100 |
| 60% | 89.6 | 62.5–100 | 70.8 | 37.5–100 |
| 70% | 83.3 | 50–100 | 75 | 50–100 |
| 80% | 77.08 | 50–100 | 75 | 50–100 |
| 90% | 70.8 | 50–100 | 79.2 | 50–100 |

TABLE 6

Sensitivity and specificity of the gas sensor instrument based on the artificial neural network interpretation of the air contaminants sensor output

| Interpretation by the ANN | Air Contaminants Sensor | | | |
|---|---|---|---|---|
| Probability of EC O157:H7 Considered Positive | Mean Sensitivity (%) | Sensitivity Range (%) | Mean Specificity (%) | Specificity Range (%) |
| 50% | 85.4 | 75–100 | 68.75 | 50–87.5 |
| 60% | 83.3 | 62.5–100 | 68.75 | 50–87.5 |
| 70% | 72.9 | 50–87.5 | 70.83 | 50–87.5 |
| 80% | 68.6 | 50–87.5 | 72.92 | 50–87.5 |
| 90% | 58.3 | 37.5–87.5 | 83.33 | 62.5–100 |

TABLE 7

Sensitivity and specificity of the gas sensor instrument based on the artificial neural network interpretation of the alcohol sensor output

| Interpretation by the ANN | Alcohol Sensor | | | |
|---|---|---|---|---|
| Probability of EC O157:H7 Considered Positive | Mean Sensitivity (%) | Sensitivity Range (%) | Mean Specificity (%) | Specificity Range (%) |
| 50% | 81.3 | 62.5–100 | 62.5 | 37.5–87.5 |
| 60% | 70.8 | 50–100 | 64.6 | 50–87.5 |
| 70% | 70.8 | 50–100 | 68.8 | 50–87.5 |
| 80% | 70.8 | 50–100 | 68.8 | 50–87.5 |
| 90% | 62.5 | 50–100 | 70.8 | 50–87.5 | this sensor may be important in future investigations using other organisms. The difference seen between the gas patterns of the *E. coli* O157:H7 isolates and the non-O157:H7 isolates is likely due to genetically coded differences in metabolic pathways. Differences in *E. coli* metabolism are already taken advantage of in routine differentiation of *E. coli* O157:H7 from non-O157:H7 *E. coli* by biochemical assays (Moat and Foster, 1995; Ratnam et al., 1988).

The sensitivity and specificity of differentiating *E. coli* O157:H7 from non-O157:H7 *E. coli* could be altered depending on what probability level was used as a cut off point. For each gas sensor, as the probability cut off point was lowered the sensitivity of detecting *E. coli* O157:H7 increased (Tables 5, 6 and 7). However, specificity decreased resulting in more non-O157:H7 *E. coli* being misclassified as *E. coli* O157:H7. Sensitivity is the number of "true positives", or signatures from *E. coli* O157:H7, correctly identified, while specificity is determined by correct classification of "true negatives" or non-O157:H7 *E. coli* gas signatures. With a greater sensitivity, there is a greater probability of correctly identifying *E. coli* O157:H7 isolates, but with a lower specificity there is an increased occurrence of "false positives" or incorrect classification of non-O157:H7 *E. coli* isolates. Deciding which probability cut off is most appropriate is dependent on the goal of the screening procedure. If it is important to detect as many *E. coli* O157:H7 isolates as possible, even if some non-O157:H7 *E. coli* isolates are falsely classified, then setting the probability at a point which maximizes sensitivity is warranted. If misclassification of non-O157:H7 *E. coli* as *E. coli* O157:H7 is undesirable, then setting the probability at a point which maximizes the specificity is most appropriate.

There are a number of limitations involved with this initial study which include: isolates were grown and monitored in only one type of media; only laboratory isolates were obtained for experimental runs; a limited number of isolates were monitored; only pure cultures were monitored; and a second sensing instrument was not used to reproduce and validate the results. Expanded studies, with further refinement of the sensor instrument, may prove that electronic nose technology is beneficial in monitoring multiple *E. coli* cultures and identifying isolates as *E. coli* O157:H7 based on the pattern of gas emissions.

This work demonstrates the potential application of electronic nose technology to enhance pre-harvest food safety efforts and aid in the rapid and economical identification of *E. coli* O157:H7. Because generic *E. coli* is part of the normal microbial flora in the intestinal track of cattle, one of the difficulties in studying the relationship between cattle and pathogenic *E. coli* is the differentiation of O157:H7 strains from the numerous other strains. In addition to pre-harvest applications, there are opportunities for this type of technology in both the food industry and human medicine.

EXAMPLE 3

Experimental Use of a Gas Sensor Based Instrument for Differentiation of *E. Coli* O157:H7 from Non-O157:H7 *E. Coli* Field Isolates Introduction

*Escherichia coli* (*E. coli*) O157:H7 has been recognized as a significant bacterial pathogen associated with potentially severe illness in humans (Padhye and Doyle., 1992). The association of *E. coli* O157:H7 with commonly consumed foods, such as ground beef, has made it an important public health concern (Doyle et al., 1997). The association of *E. coli* O157:H7 with ground beef has led to the identification of cattle as a reservoir for the organism (Buchanan and Doyle, 1997; Padhye and Doyle., 1992). Recent pre-harvest food safety efforts have emphasized identifying the ecological association of *E. coli* O157:H7 with cattle or within cattle production systems (Hancock et al., 1998). Because generic *E. coli* is part of the normal intestinal flora of ruminants (Gyles, 1994), *E. coli* O157:H7 must be differentiated in research efforts. Currently, detection and differentiation techniques are often time consuming, expensive, and lack sensitivity (Doyle et al., 1997). The development of a diagnostic tool that is more economically feasible, easy to use, and time and labor efficient could prove valuable in enhancing pre-harvest food safety research.

Artificial olfactory technology is finding increasing application for differentiating odors and various volatile compounds (Gardner et al., 1998; Keshri et al., 1998; Lane and Wathes, 1998). Artificial olfactory technology is usually based on the use of metal oxide gas sensors to detect and measure volatile compounds coupled with an artificial neural network (ANN) or pattern recognition program for data interpretation (Bartlett et al., 1997). The gas sensors detect volatile compounds and generate a gas signature, which is interpreted by the ANN. Recent advances with this instrumentation have found application in the food industry for detecting rancidity, spoilage, and "off" odors (Bartlett et al., 1997). This technology has also been studied for its application in differentiating various species of bacteria and fungi (Gardner et al., 1998) (Keshri et al., 1998).

In a previous investigation, a gas sensor based instrument was developed and evaluated for use as a tool for differentiating E. coli O157:H7 from non-O157:H7 E. coli (Younts, 1999a). This investigation involved the development of a gas sensor based instrument for the differentiation of E. coli O157:H7 from non-O157:H7 E. coli by detecting unique gas emission patterns. Initial evaluation of this technology involved monitoring the gas emissions of eight E. coli isolates, four isolates of E. coli O157:H7 and four non-O157:H7 E. coli isolates, cultured in a laboratory setting. Standard gas signatures were generated from these isolates and analyzed by an artificial neural network (ANN) (Younts et al., 1999a). The ANN was used to recognize and classify the gas signatures as E. coli O157:H7 or non-O157:H7 E. coli. The system was evaluated based on its ability to correctly classify the organisms. Based on visually observable differences between the gas signatures of E. coli O157:H7 and non-O157:H7 E. coli and the accuracy of the ANN in classifying the bacteria, this technology showed potential for further development. A limitation in the initial investigation was that only lab isolates were monitored. The purpose of this study was to further test the combined ability of the gas sensor instrument and the ANN to differentiate isolates of E. coli O157:H7 from non-O157:H7 E. coli using field isolates from cattle, cattle environments, and human clinical outbreaks.

Materials and Methods

Instrumentation

In a previous investigation, an instrument was assembled for collecting, monitoring, and recording the gas emissions from various growing E. coli cultures (Younts et al., 1999b). This instrument was designed to allow for culturing of bacteria, collection or capture of gas emissions, detection and identification of the gases or volatile compounds, and recording of the data. A sensor chamber was built containing an array of 4 metal oxide gas sensors (Figaro USA, Inc., Glenview, Ill.), a temperature sensor, and a humidity sensor (Younts et al., 1999b). The sensors in this chamber or instrument were chosen based on their capability to detect common volatile breakdown products of bacterial metabolism (Moat and Foster, 1995). Table 8 shows the sensor type, target compounds it detects, and sensitivity.

TABLE 8

Sensors employed in instrument with detectable compound specificity and sensitivity levels

| Gas Sensors | Specific Compounds | Sensitivity |
|---|---|---|
| TGS 826 Ammonia | Ammonia, amines | 30 ppm |
| TGS 822 Alcohol | Methane, iso-butane, ethanol | 50–5000 ppm |
| TGS 800 Air Contaminants | Methane, iso-butane, ethanol | 1–10 ppm |
| TGS 825 Hydrogen Sulfide | Hydrogen Sulfide | 5 ppm |

The gas sensors are designed to detect specific volatile compounds; the presence of the specific compounds causes electrical conductivity within the sensor to increase. The electrical signals generated by this increased conductivity are acquired by a data acquisition board and converted to voltage readings. A computer software program, (MeterBOSS, Teramar Group, Inc., El Paso, Tex.), was used to record and continuously plot the voltage readings, generating the gas signatures.

Field Isolate Collection

Twenty E. coli isolates were obtained from the Bacteriology Laboratory at the Veterinary Diagnostic Center, University of Nebraska. Most of the isolates were collected as part of an ongoing animal production food safety investigation in Midwestern feedyards. Additional isolates were obtained from an outbreak of human illness due to E. coli O157:H7 and contaminated venison. These isolates had been characterized using biochemical reactions in selective culturing, latex agglutination, and polymerase chain reaction (PCR). Of the twenty isolates, 12 were confirmed as E. coli O157:H7.

Culturing and Collection of Gas Signatures

Procedures for the bacteria culturing and collection of gas signatures were performed as previously defined (Younts, 1999b). All isolates were grown in nutrient broth to create stock cultures. The bacteria concentration in the stock cultures was determined by viable plate count procedures. All culturing was performed in a certified Biological Safety Level II laboratory. One experimental run, generating a gas signature, was completed for each isolate using previously described procedures (Younts 1999a). For each run, 10 ml of nutrient broth was placed in a sterile 14 ml polystyrene vial and inoculated with $10^5$ colony forming units/ml of the isolate. The vial was centrally placed in a 37±0.2° C. dry block heater and the sensor chamber positioned on the heater over the culture vial. Each isolate was grown for 16 hours with gas measurements taken every 5 minutes.

Gas Signature Interpretation

The gas signatures were interpreted by visual observation and computer analysis. Based on the general shape, the gas patterns were visually evaluated for characteristic differences and similarities compared to the original gas signatures from eight laboratory isolates previously studied (Younts, 1999b). For artificial neural network (ANN) (BrainMaker, California Scientific Software, 1998) interpretation, 32 E. coli gas signatures generated from the previous study (Younts et al., 1999a) were used to train the ANN for pattern recognition. In the training process the ANN was configured for pattern recognition and data classification. Gas signatures from all 20 field isolates were subject to interpretation and classification by the trained ANN. Each of the gas signatures, in both the training and testing data, were then normalized using the following equation:

$$y = \frac{(Xi) - Xmin}{Xmax - Xmin}$$

Xi=voltage data point i=1, . . . , n for all data for each sensor

Xmax=the highest voltage point

Xmin=the lowest voltage point

This method of normalization was used to reduce variation in the gas patterns due to background voltage levels or pattern height. Following normalization, the ANN was retrained with the original 32 gas signatures and then tested with the 20 field samples. The ANN determines a probability that the isolate being tested is *E. coli* O157:H7 or non-O157:H7 *E. coli*. For this study, an isolate was classified as *E. coli* O157:H7 or non-O157:H7 *E. coli* based on which probability was highest. For example, if the isolate being tested had a greater probability of being *E. coli* O157:H7 than non-O157:H7 *E. coli*, it was classified as *E. coli* O157:H7.

Test Accuracy

Based on the results of the gas signature interpretation by the artificial neural network using both the normalized and non-normalized data, the sensitivity and specificity of the instrument for differentiating *E. coli* O157:H7 from non-O157:H7 *E. coli* was determined (Smith, 1995).

Results

Gas Signature Observations

Figure 14:
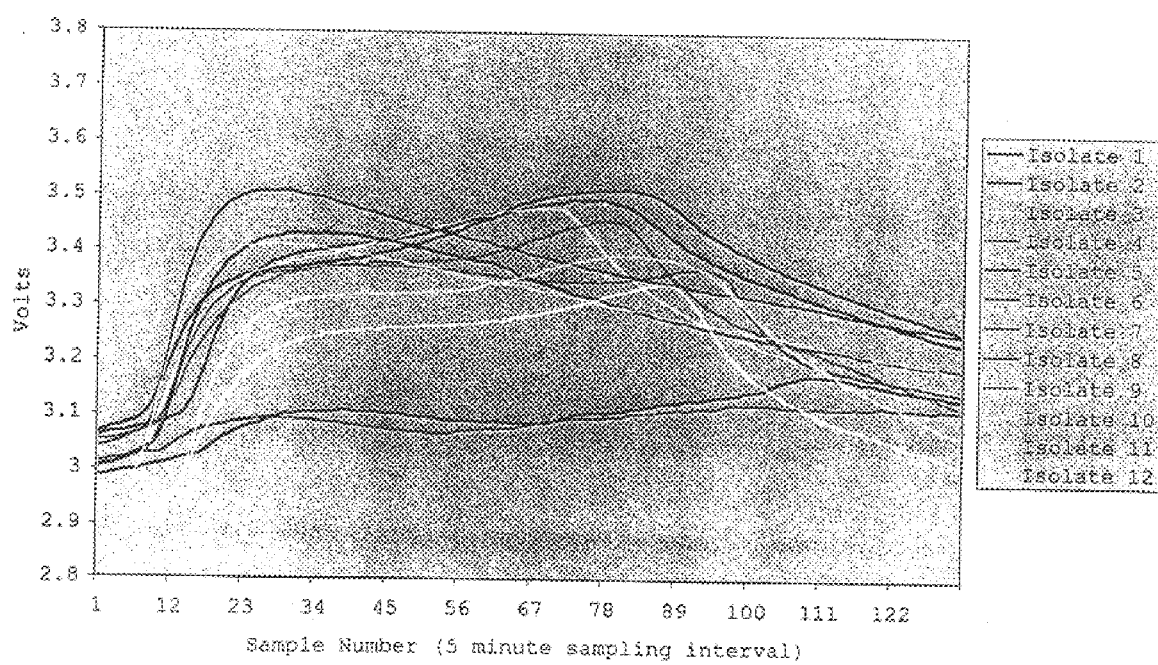
FIG. 14 is a graph of gas signatures from the ammonia sensor for each of the E. coli O157:H7 field isolates.
Figure 15:
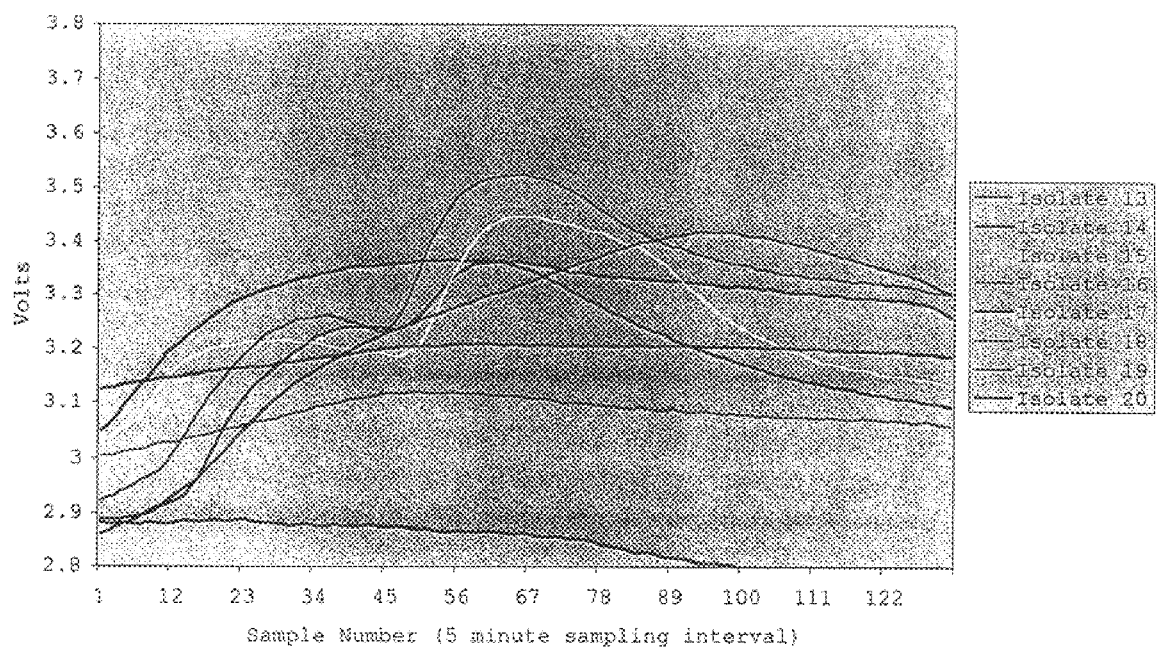
FIG. 15 is a graph of gas signatures from the ammonia sensor for each of the non-O157:H7 E. coli field isolates.
Figure 16:
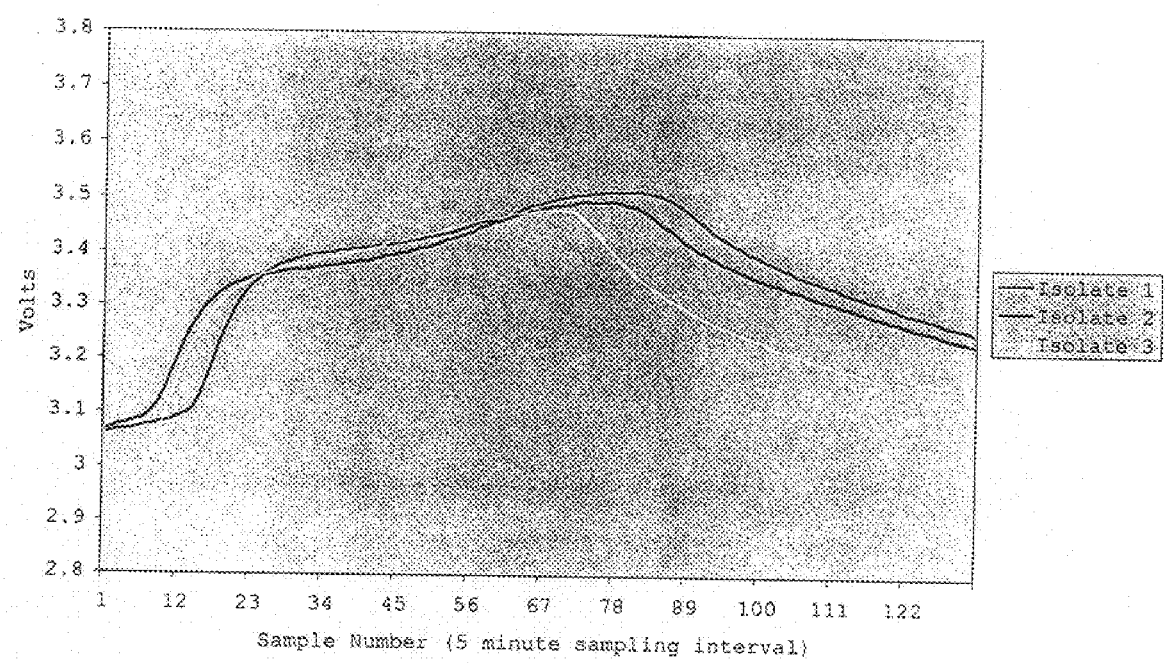
FIG. 16 is a graph of gas signatures from the ammonia sensor for E. coli O157:H7 field isolates from outbreak of human illness.
Figure 17:
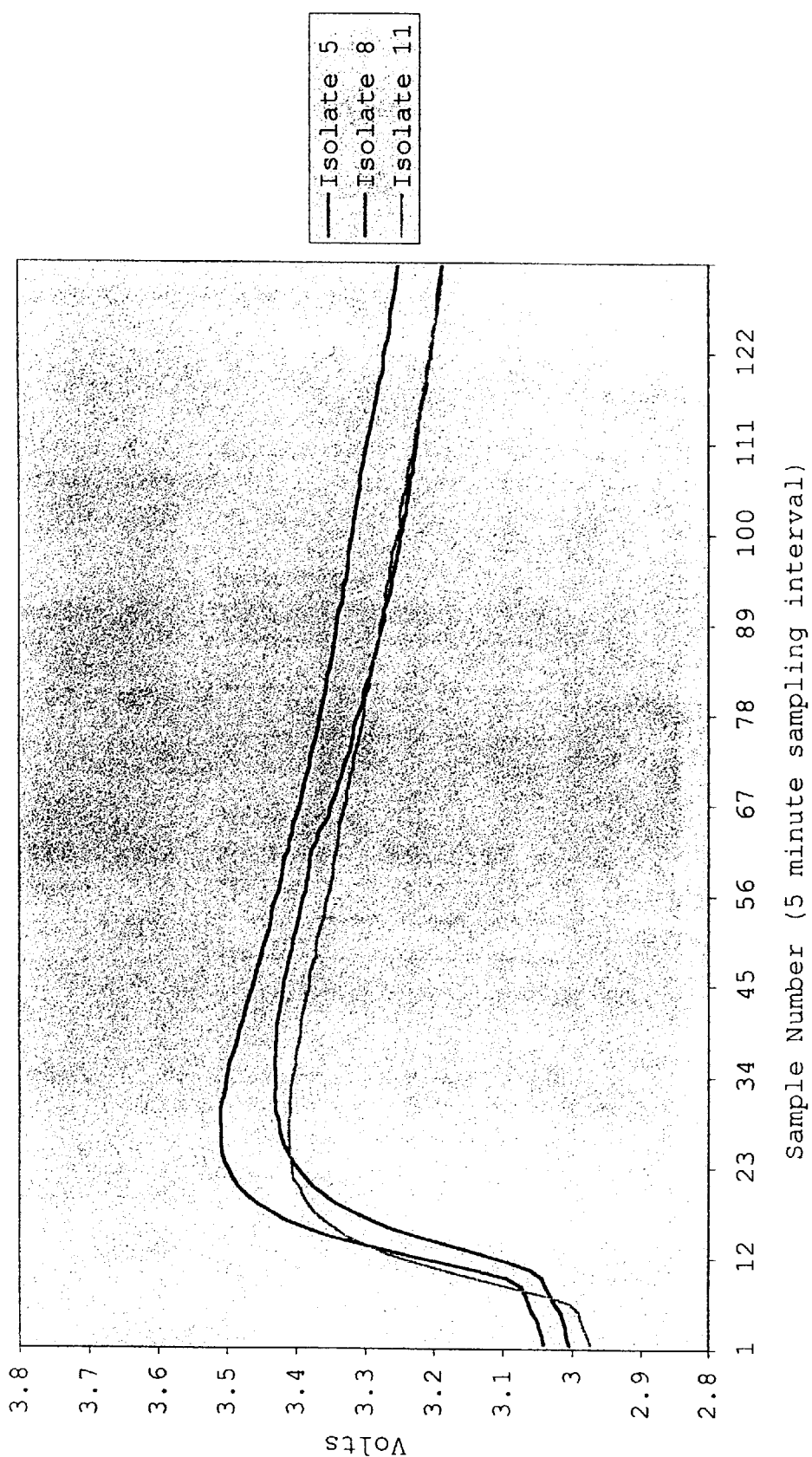
FIG. 17 is a graph of gas signatures from the ammonia sensor for E. coli O157:H7 isolates from the same feed yard.
Figure 18:
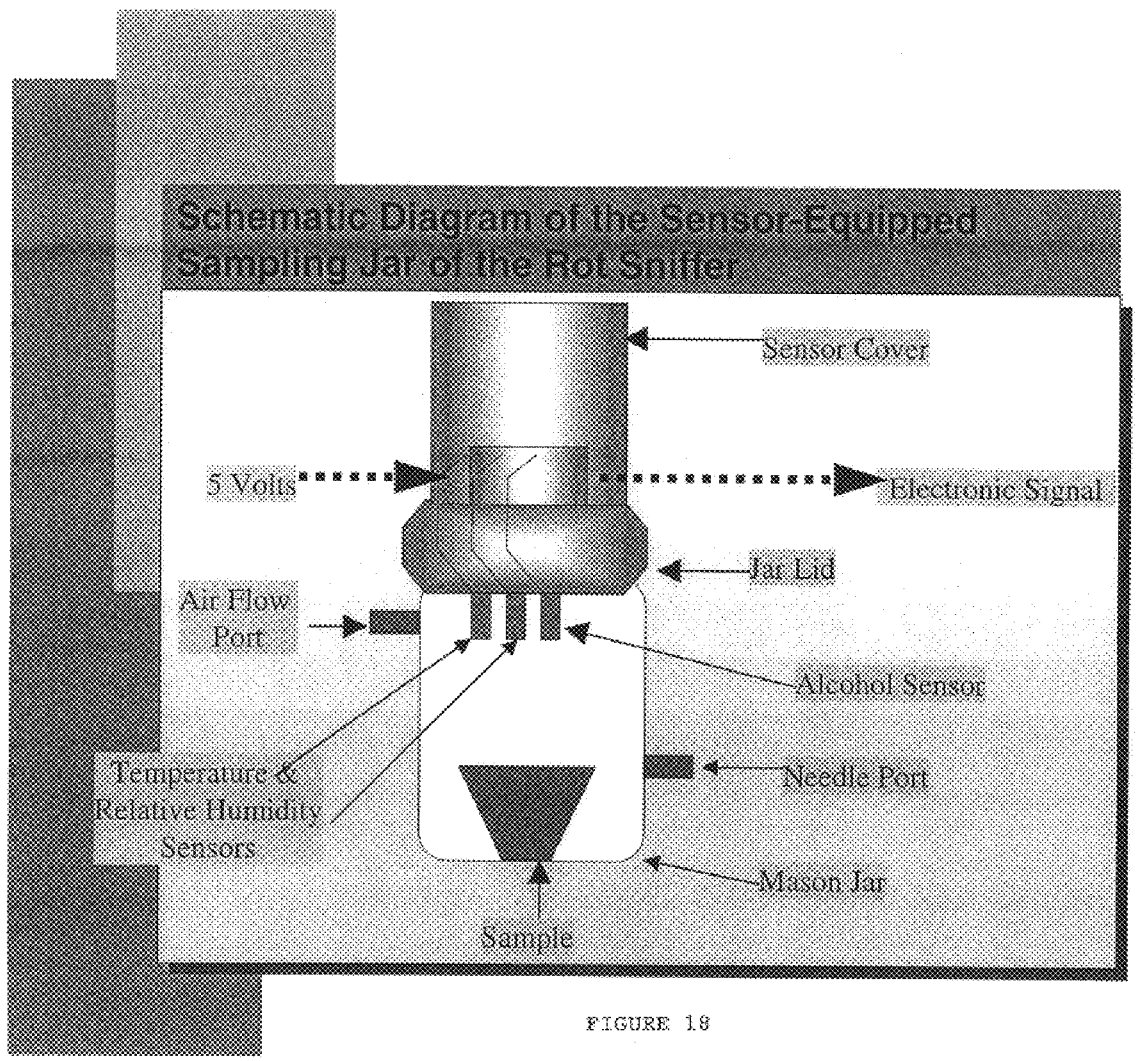
FIG. 18 is a schematic diagram of the apparatus used as a rot sniffer.
Figures 18A, 18B:
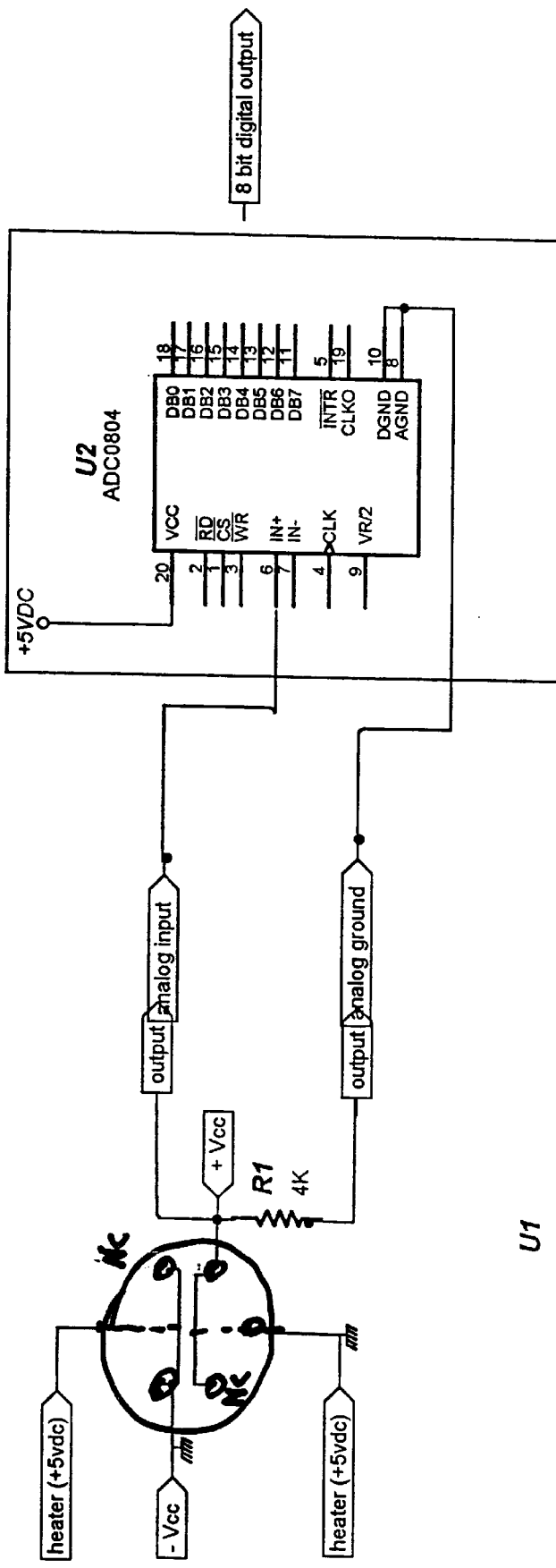
FIG. 18A shows the diagram for the TGS 822 (Figaro, Japan) sensor (transducer) and B&B 232 SDA12 A to D converter.
FIG. 18B shows the heater circuit.

As seen previously, the ammonia, air contaminants and alcohol sensors detected gases over time, indicative of volatile breakdown products of bacterial growth and metabolism. Many of the gas signatures shared shape characteristics similar to either the standard *E. coli* O157:H7 or non-O157:H7 *E. coli* isolates initially tested. However, there was a greater variation in the overall form of the gas signatures, presumably due to strain variation. The greatest variation in gas signatures was observed among the non-O157:H7 isolates. All of the gas signatures from *E. coli* O157:H7 isolates shared some general characteristics; however, visually discernible differences in the *E. coli* O157:H7 gas signatures were observed. FIGS. 14 and 15 show the gas signatures from the ammonia sensor for each of the *E. coli* O157:H7 and non-O157:H7 *E. coli* field isolates, respectively. Interestingly, *E. coli* O157:H7 isolates obtained from similar sources produced gas signatures that were visually most closely alike. For example, the isolates obtained from the outbreak of human illness had very similar signatures (FIG. 16). Isolates that were obtained from the same feedlots, at different times and different locations, also showed the same pattern of gas emissions (FIG. 17).

Artificial Neural Network Analysis

Contingency tables showing the frequency of correct classification of the *E. coli* (EC) isolates by the ANN based on the gas signatures from the ammonia, air contaminants and alcohol sensors using non-normalized data are shown in Table 9.

TABLE 9

Contingency tables showing the results of ANN classification of field isolates using non-normalized data

| | True Type O157:H7 | Non-O157:H7 | | |
|---|---|---|---|---|
| Ammonia | | | | |
| O157:H7 | 6 | 4 | Sensitivity | 50% |
| Non-O157:H7 | 6 | 4 | Specificity | 50% |
| Air Contaminants | | | | |
| O157:H7 | 5 | 4 | Sensitivity | 41.70% |
| Non-O157:H7 | 7 | 4 | Specificity | 50% |
| Alcohol | | | | |
| O157:H7 | 5 | 4 | Sensitivity | 41.70% |
| Non-O157:H7 | 7 | 4 | Specificity | 50% |

The frequency of correct classification of *E. coli* isolates using normalized data are shown in the contingency tables in Table 10.

TABLE 10

Contingency tables showing the results of ANN classification of field isolates using normalized data

| | True Type O157:H7 | Non-O157:H7 | | |
|---|---|---|---|---|
| Ammonia | | | | |
| O157:H7 | 11 | 4 | Sensitivity | 91.7% |
| Non-O157:H7 | 1 | 4 | Specificity | 50% |
| Air Contaminants | | | | |
| O157:H7 | 12 | 5 | Sensitivity | 100% |
| Non-O157:H7 | 0 | 3 | Specificity | 37.5% |
| Alcohol | | | | |
| O157:H7 | 11 | 4 | Sensitivity | 91.7% |
| Non-O157:H7 | 1 | 4 | Specificity | 50% |

Discussion

Gas sensor based technology, in conjunction with an ANN, has previously been used to differentiate between classes of bacteria (Gardner et al., 1998). In a previous study (Younts et al., 1999b) a gas sensor instrument was developed to differentiate *E. coli* O157:H7 from non-O157:H7 *E. coli* based on unique gas signatures generated during bacterial growth in laboratory cultures. Using a limited number of characterized *E. coli* O157:H7 and non-O157:H7 isolates (n=8), gas signatures were generated and analyzed by an ANN. The sensitivity and specificity of this system ranged from 81–92% and 63–71% respectively, depending on the types of gas sensor signature analyzed.

In this invention the gas sensing instrument was evaluated for its ability to aid in the identification of *E. coli* O157:H7 and non-O157:H7 isolates obtained from various field situations, including those associated with an outbreak of clinical human illness and from multiple cattle production systems. Greater variation in the bacteria strains and patterns of gas emissions made the correct classification of the field isolates using the ANN less accurate. Although the overall shape of the gas signatures showed some variation, the isolates of *E. coli* O157:H7 shared some general visual characteristics. Greater conformity of the gas signatures of the *E. coli* O157:H7 isolates was seen when the isolates were sorted by source. For example, isolates originating from an outbreak of human illness had virtually identical gas signatures. Isolates obtained from the same feedlot, at different times and from different environmental samples, also had visually similar gas signatures. Similarities in gas patterns of *E. coli* O157:H7 obtained from the same source may be an indication of relatedness. Based on this observation, unique gas signatures generated by individual strains of *E. coli* O157:H7 may have value as an epidemiological tool for determining the relatedness of different *E. coli* O157:H7 isolates. The non-O157:H7 isolates generated a greater variety of gas signature patterns as more serotypes were represented. The differences between gas signatures from different serotypes could result from the presence or absence of various metabolic processes.

Using an ANN to analyze the gas signatures, a much lower sensitivity and specificity was seen for predicting the class of the field isolates than was observed previously using a limited number of laboratory isolates. However, the sensitivity of the system greatly improved when the data was normalized. Pattern recognition by the ANN is accomplished by comparing voltage readings at each time point during the culture period. Normalizing the data eliminates wide variation in voltage levels that may confuse the ANN. By normalizing the data, interpretation of the gas signatures can be made based more on the shape of the gas curves rather than on specific voltage levels. From the results of the pattern interpretation, it was determined that a larger training set representing more non-O157:H7 *E. coli* serotypes was needed for training the ANN to more accurately classify non-O157:H7 *E. coli* isolates. However, with the limited training set, *E. coli* O157:H7 can be detected with a high degree of sensitivity, indicating greater similarity of the *E. coli* O157:H7 gas signatures.

Further refinement of the instrument and parameters for pattern interpretation can increase the sensitivity and specificity of the instrument and ANN for classifying *E. coli* isolates. Pattern recognition needs to be focused on determining the most distinctive characteristics of the gas signatures of *E. coli* O157:H7 isolates. Additional methods of data normalization for the output from gas sensor instruments may exist that will improve the accuracy of the ANN. These means of normalizing the data may serve to eliminate specific types of differences between the gas signatures, making pattern recognition by the ANN easier. An analytical program also needs to allow for greater variation in the gas patterns seen with the numerous non-O157:H7 serotypes. Through further development of an analytical tool for interpreting the gas signatures and ways of normalizing the data, the diagnostic value of the gas sensor based technology could be greatly improved.

Culturing and Collection of *E. coli* Gas Signatures
To Start
1. Turn on dry block heater and set to 37° C.
2. Turn on computer and open MeterBOSS (Teramar Group, Inc., El Paso, Tex.) program
3. In MeterBOSS, go to Data Record, click Data Plot
4. On screen, click Filename field, enter file name for experiment
5. Next click Time Log Interval field, enter desired rate of gas sampling (5 minutes for standard *E. coli* experiments)
Working in a Biohazard Hood
6. Aseptically transfer 10 ml of nutrient broth (Difco Laboratories, Detroit, Mich.) to a sterile 14 ml polystyrene vial (Falcon 352057, Becton Dickinson Labware, Franklin Lakes, N.J.)
7. Inoculate vial with desired bacteria concentration ($10^5$ CFU's/ml for standard *E. coli* experiments) using a sterile pipette
8. Place the open, inoculated vial in the rear center well of the dry block heater
9. Settle the sensor chamber centrally over the heater block with the center hole in the chamber base plate over the vial To Start Sampling
10. On screen, click Setup Complete to start gas sampling
    Do not exit MeterBOSS Data Display Screen or sampling will be discontinued
11. Let system run for desired length of sampling (16 hours for standard *E. coli* experiments)

To End
12. Exit MeterBOSS, moving pointer to top of screen will display menu, EXIT
13. Lift sensor chamber and remove vial
14. Add nolvassan solution to the vial, seal and discard in biohazard waste container
15. Turn off dry block heater Establishing Growth Curves
To Start
1. Turn on dry block heater and set to 37° 1 C.
2. Aseptically transfer 10 ml of nutrient broth (Difco Laboratories, Detroit, Mich.) to a sterile 14 ml polystyrene vial
3. Inoculate vial with desired bacteria concentration ($10^5$ CFU's/ml for standard *E. coli* experiments) using a sterile pipette
4. Place the open, inoculated vial in the rear center well of the dry block heater
5. Using a sterile pipette, pull 100 µl of sample culture and transfer to 10 ml of nutrient broth in a polystyrene vial (1:100 dilution)
    vortex vial approx. 20 seconds
    transfer 10 µl to each of 2 plates, spread, incubate inverted at 37° C.
6. Settle the sensor chamber centrally over the heater block with the center hole in the chamber base plate over the vial At 2 & 4 HOURS
7. Prepare 2 sterile polystyrene vials with 10 ml of nutrient broth each
8. Lift the sensor chamber, Pull 100 µl from sample and transfer to first vial (1:100 dilution)
    vortex and transfer 100 µl to second vial (serial dilutions) (1:10,000 dilution)
    and transfer 10 µl to each of 2 plates, spread
9. From second vial, transfer 10 µl to each of two plates, spread, and incubate
10. Replace sensor chamber At 6, 8, 10, 12, 14, & 16 HOURS
11. Prepare 3 vials with 10 ml of nutrient broth each
12. Pull 100 µl from sample and transfer to first vial (1:100 dilution)
    vortex and transfer 100 µl to second vial (1:10,000 dilution)
13. Vortex second vial and transfer 100 µl to third vial and 10 µl to each of 2 plates (1:1,000,000 dilution), spread
14. Vortex third vial and transfer 10 µl to each of 2 plates, spread, incubate
15. Count plates 12–24 hours after incubation Creating Stock Cultures and Determining Concentration
To Create Stock Cultures of *E. coli*
1. Aseptically transfer *E. coli* isolate to 10 ml of nutrient broth (Difco Laboratories, Detroit, Mich.) in a sterile 14 ml polystyrene vial ( )

2. Incubate inoculated vial for 12–24 hours at 37° C.

To Determine Stock Culture Concentration

3. Prepare 3 vials with 10 ml of nutrient broth each
4. Pull 100 µl from stock culture and transfer to first vial (1:100 dilution)
   vortex and transfer 100 µl to second vial (1:10,000 dilution)
5. Vortex second vial and transfer 100 µl to third vial and 10 µl to each of 2 plates (1:1,000,000 dilution), spread
6. Vortex third vial and transfer 10 µl to each of 2 plates, spread, incubate
7. Count plates 12–24 hours after incubation
8. Back calculate 10-fold dilutions for every step to determine original stock culture concentration

EXAMPLE 4

The current method of detecting soft-rot in potato storage bins consists of visual inspection and odor detection by bin managers. This type of inspection is greatly limited by the thresholds of human senses; often infections are not discovered until considerable damage has been done. These limitations can be overcome by the use of an electronic nose. This example shows the effectiveness of the potato sniffer, a laboratory model electronic nose, as a potential early-warning diagnostic tool for soft-rot disease. Amount of rot damage and volatile emissions correlate highly with voltage readings. Results from gas chromatography and mass spectrometry show high levels of acetone, 2-propanol, 1-butanol, and dimethyl disulfide from diseased tubers. Dimethyl sulfide, 2-butanol, and 1-propanol have also been consistently recorded in all the samples. The potato sniffer measures volatile emissions at very low concentrations. The development of a cost-effective, real-time, potato sniffer to monitor the spread of soft rot disease in potato storage piles will allow bin managers to detect early rotting and implement intervention strategies before economic losses become great.

Materials and Methods

Instrumentation

Six sampling units of the potato sniffer were built, each containing an alcohol, relative humidity, and temperature sensor. The sensors were connected to a data acquisition system. When exposed to a volatile, the outputs of the sensors were changed into electronic signals, and sent to the data acquisition system. These signals were read and quantified as a number between 0 and 5 volts. The system allowed to project a real-time graph of all the sensor outputs, giving a constantly updated picture of the relative concentration of volatiles, and relative humidity and temperature of the headspace gas.

Instrument Validation

The precision, accuracy, and reproducibility of the potato sniffer were established. This stage of the experiment was designed to find any correlation between the concentration of the volatiles in the headspace and the voltage output of the potato sniffer. Ethanol, acetone, and 2-propanol standards of varying concentrations were used to validate the sensitivity of the potato sniffer. The headspace concentration ($C_{headspace}$) of the liquid standard can be estimated using equation (1), where S is the concentration of the alcohol solution (in ppm) and T is the temperature (in degrees Celsius) (Harger et al., 1950).

$$C_{headspace} = 0.01442 \left(2.316^{\frac{T}{10}}\right) S \quad (1)$$

For example, to achieve a headspace acetone concentration of 50 ppm, 57.9 mg of 99.9% liquid acetone were added to 100 ml of distilled water. The standard solutions were placed in glass jars and positioned inside the sampling units for about one hour to reach headspace equilibrium before voltage readings were taken. One of the sensors was designated the control, and measured only the output from distilled water. The data was logged and analyzed for correlation between headspace concentration (ppm) and voltage output. A gas chromatograph (GC) was used to corroborate the calculated and measured concentrations of the ethanol standards.

Sniffing for Soft Rot

Inoculum of *Erwinia carotovora* var *carotovora* was prepared from overnight cultures of the bacterium grown in LB broth. The culture was diluted with 0.1 M $MgSO_4$ and adjusted to a concentration of approximately $10^8$ colony forming units (cfu) per ml by measuring the absorbance of the bacterial suspension at 610 nm with a spectrophotometer. Assortments of Snowden potatoes were then inoculated with *E. carotovora* by pipetting 0.1 ml of the fluid culture and stabbing it 1.5 cm into the potatoes with a disposable pipette tip as described by Maher and Kelman (1983). Control potatoes were similarly stabbed with empty pipette tips. The pipette tips were left in place. Once inoculated, the infected potatoes were placed into the sampling units. Data were collected on each set of the infected potatoes every 30 minutes for seven days. This allowed the *E. carotovora* infection to peak and level off. The volatiles emitted by the infected potatoes were logged and quantified. After one week, the production of volatiles by the infected potato had leveled and the potatoes were removed. The infected tissue was then excised and weighed.

Results and Discussion

Figure 19:
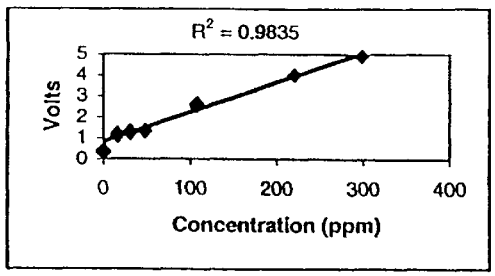
FIGS. 19 to 24 are graphs showing results with a potato sniffer apparatus.
Figure 20:
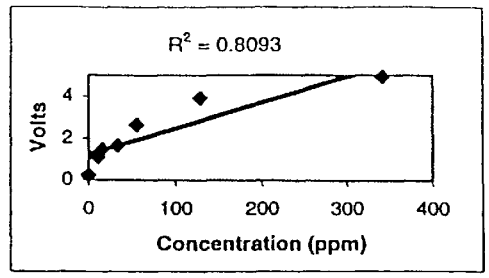
Figure 21:
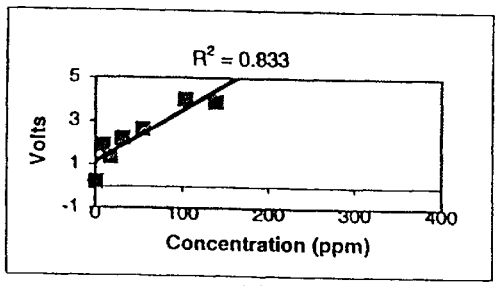
Figure 22:
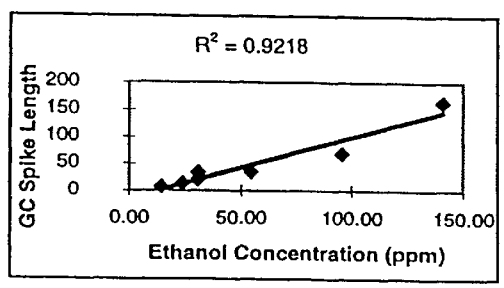
Figure 23:
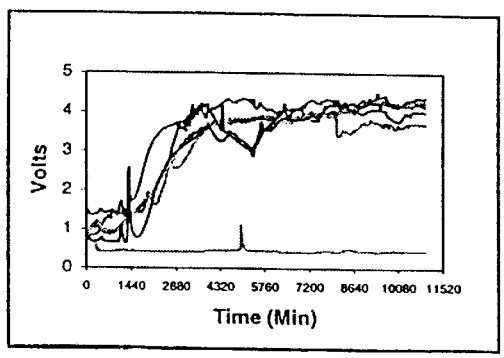

The potato sniffer showed a linear relationship between ethanol, acetone, and 2-propanol headspace concentrations and voltage output (FIGS. 19, 20). FIG. 21 shows a sample gas chromatograph (GC) validation of the ethanol standard solution. The zero of the volatile sensor averaged approximately 0.2 volts. A five volt reading was achieved for about 300 ppm of 2-propanol and ethanol, and 150 ppm for acetone. The real-time potato sniffer voltage readings of the infected potatoes vs. a control (non-infected potato) reveal a significant difference in the amount of headspace volatiles produced. Sample data is shown in FIG. 22 with the control (non-infected potato) as a straight line, having an average voltage reading of approximately 0.5 over time. The five infected potatoes registered a logistic increase in voltage reading over time.

Figure 24:
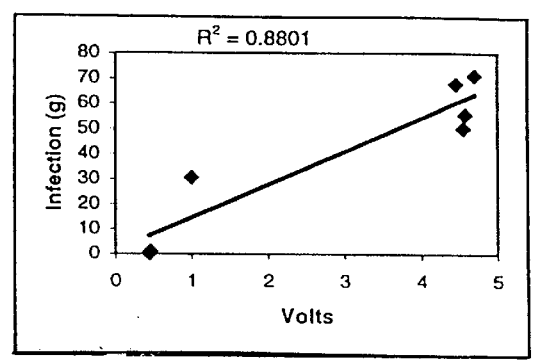

The amount of soft rot infection of the potato tuber was evaluated by measuring the mass of the rotted tissue (in grams). The potato sniffer revealed a linear correlation between the amount of infection and the voltage output of the sensors (FIG. 24), indicating that the level of soft-rot infection in the potatoes is directly correlated to headspace volatile concentrations.

Gas chromatography/mass spectrometer (GC/MS) was used to identify the chemical composition of the volatiles recorded by the potato sniffer. The GC/MS results showed high concentrations of dimethyl disulfide, acetone, 2-propanol, 1-butanol, and carbon dioxide.

Conclusion

Voltage reading by the potato sniffer correlates highly with volatile concentrations and rotted tissues in diseased potato tubers. GC/MS analysis of the headspace gases reveals high levels of dimethyl disulfide, acetone, 2-propanol, 1-butanol, and carbon dioxide from *E. carotovora*-infected potatoes. Differences observed in the voltage readings for a gradient of potato infection illustrate the potential of the potato sniffer to identify the degree of soft-rot infection of potato tubers through their volatile emissions. Using the potato sniffer will be quick and simple without any special training or experience. Implementation of the potato sniffer will be advantageous to potato farmers and distributors. If potatoes in storage are detected with a very low thresh-hold amount of bacterial damage, the tubers may still be useable for some purposes. Thus the potato sniffer will save time, money, and waste by providing a low-cost volatile detection system that will allow for a rapid, continuous monitoring of volatile production in real-time in potato storage bins.

REFERENCES

Alocilja, E. 1998. Personal Communications.

Atlas, R. M. 1995. Principles of Microbiology. Mosby-Year Book, Inc. St. Louis, Mo.

Bartlett, P. N., J. M. Elliot, and J. W. Gardner. 1997. Electronic noses and their application in the food industry. Food Technology 51:44–48.

Boyce, T. G., D. L. Swerdlow, and P. M. Griffin. 1995. *Escherichia coli* O157:H7 and the hemolytic uremic syndrome. New England Journal of Medicine 333: 364–368.

Brown, C. A., B. G. Harmon, T. Zhao, and M. P. Doyle. 1997. Experimental *Escherichia coli* O157:H7 carriage in calves. Applied and Environmental Microbiology 63: 27–32.

Buchanan, R. L., and M. P. Doyle. 1997. Foodborne disease significance of *Escherichia coli* O157:H7 and other enterohemorrhagic *E. coli*. Food Technology 51: 69–76.

Cray, W. C., and H. W. Moon. 1995. Experimental infection of calves and adult cattle with *Escherichia coli* O157:H7. Applied and Environmental Microbiology 61: 1586–1590.

Dargatz, D. A., S. J. Wells, L. A. Thomas, D. D. Hancock, and L. P. Garber. 1997. Factors associated with the presence of *Escherichia coli* O157 in feces of feedlot cattle. Journal of Food Protection 60: 466–470.

Diez-Gonzalez, F., T. R. Callaway, M. G. Kizoulis, and J. B. Russell. 1998. Grain feeding and the dissemination of acid-resistant Escherichia coli from cattle. Science 281: 1666–1668.

Doyle, M. P., L. R. Beuchat, and T. J. Montville, eds. 1997. Food Microbiology: Fundamentals and Frontiers. Washington, D.C.: American Society for Microbiology.

Figaro USA, I. Product Information Guide Figaro USA, Inc, February, 1996.

USDA-FSIS. 1998. Report to Congress, Foodnet: An Active surveillance system for bacterial foodborne diseases in the United States. Washington, D.C.

Garber, L. P., S. J. Wells, D. D. Hancock, M. P. Doyle, J. Tuttle, J. A. Shere, and T. Zhao. 1995. Risk factors for fecal shedding of *Escherichia coli* O157:H7 in dairy calves. Journal of the American Veterinary Medical Association 207: 46–49.

Gardner, J. W., M. Craven, C. Dow, and E. L. Hines. 1998. The prediction of bacteria type and culture growth phase by an electronic nose with a multi-layer perceptron network. Measurement Science and Technology 9:120–127.

Gyles, C. L., ed. 1994. *Escherichia coli* in Domestic Animals and Humans. Wallingford: CAB International.

Hancock, D. C., T. E. Besser, D. H. Rice, E. D. Ebel, D. E. Herriott, and L. V. Carpenter. 1998. Multiple sources of *Escherichia coli* O157 in feedlots and dairy farms in the Northwestern USE. Preventive Veterinary Medicine 35: 11–19.

Hancock, D. D., D. H. Rice, L. A. Thomas, D. A. Dargatz, and T. E. Besser. 1997. Epidemiology of *Escherichia coli* O157 in feedlot cattle. Journal of Food Protection 60 (5): 462–465.

Hancock, D. C., D. H. Rice, D. E. Herriott, T. E. Besser, E. D. Ebel, and L. V. Carpenter. 1997a Efects of farm manure-handling practices on *Escherichia coli* O157:H7 prevalence in cattle. Journal of Food Protection 60: 363–366.

Keshri, G., N. Magan, and P. Voysey. 1998. Use of an electronic nose for the early detection and differentiation between spoilage fungi. Letters in Applied Microbiology 27: 261–264.

Kudva, I. T. , P. G. Hatfield, and C. J. Hovde. 1996. *Escherichia coli* O157:H7 in microbial flora of sheep. Journal of Clinical Microbiology 34: 431–433.

Lane, A. J. P., and D. C. Wathes. 1998. An electronic nose to detect changes in perineal odors associated with estrus in the cow. Journal of Dairy Science 81: 2145–2150.

March, S. E., and S. Ratnam 1986. Sorbitol-MacConkey medium for detection of *Escherichia coli* O157:H7 associated with hemorrhagic colitis. Journal of Clinical Microbiology 23: 869–872.

Moat, A. G., and J. W. Foster, 1995. Microbial Physiology (Third ed.) Wiley-Liss. New York, N.Y.

Padhye, N. V., and M. P. Doyle. 1992. *Escherichia coli* O157:H7: epidemiology, pathogenesis, and methods for detection in food. Journal of Food Protection 55: 555–565.

Ratnam, S., S. March, R. Ahmed, G. Bezanson, and S. Kasatiya. 1988. Characterization of *Escherichia coli* serotype O157:H7. Journal of Clinical Microbiology 26: 2006–21012.

Rice, D. H., D. D. Hancock, and T. E. Besser. 1995. Verotoxigenic *E. coli* O157:H7 colonization of wild deer and range cattle. The Veterinary Record 137: 524.

Sanderson, M. W., J. M. Gay, D. D. Hancock, C. C. Gay, L. K. Fox, and T. E. Besser. 1995. Sensitivity of bacteriologic culture for detection of *Escherichia coli* in bovine feces. Journal of Clinical Microbiology 33: 2616–2619.

Smith, R. D. 1995. Evaluation of Diagnostic Tests. In Veterinary Clinical Epidemiology: A Problem-Oriented Approach. Pp. 31–52 Ann Arbor, Mich.: CRC Press.

Stevenson, K. E., and D. T. Bernard, eds. 1995. HACCP Establishing Hazard Analysis Critical Control Point Programs: A Workshop Manual. Second ed. The Food Processors Institute. Washington, D. C.

Tarr, P. I. 1995. *Escherichia coli* O157:H7: Clinical, diagnostic and epidemiological aspects of human infection. Clinical Infections Disease 20: 1–10.

Thompson, J. S., D. S. Hodge, and A. A. Borczyk. 1990 Rapid biochemical test to identify veroxytotoxin-positive strains of *Escherichia coli* serotype O157. Journal of Clinical Microbiology 28: 2165–2168.

Trevena, W. B., R. S. Hooper, C. Wray, G. A. Willshaw, T. Cheasty and G. Dimingue. 1996. Vero cytotoxin-producing *Escherichia coli* O157 associated with companion animals. The Veterinary Record 142: 400.

Tuang, R. N., J. L. Rademaker, E. C. Alocilja, R. J. Louws, and F. J. de Bruijn. 1999. Identification of bacterial rep-PCR genomic fingerprints using a backpropagation neural network. FEMS Microbiology Letters 177: 249–256.

Unnevhr, L. J. , and H. H. Jensen. 1996. HACCP as a ragulatory innovation to improve food safety in the meat industry. American Journal of Agricultural Economics 78: 764–769.

Younts, S., E. Alocilja, W. Osburn, S. Marquie and D. Grooms. 1999a Development of electronic nose technology as a diagnostic tool in detection and differentation of *Escherichia coli* O157:H7. Journal of Animal Science 77 (Suppl. 1):129 (Abstr.).

Younts, S. M., D. Grooms, W. Osburn, S. Marquie, and E. Alocilja. 1999b. Differentiation of *Escherichia coli* O157:H7 From non-O157:H7 *E. coli* serotypes using a gas sensor based, computer controlled detection system. Paper presented at Institute of Biological Engineering, June, Charlotte, N.C.

Younts, S. M. 1999a. Chapter 2: Development and evaluation of a gas sensor based instrument for identifying *E. coli* O157:H7 in a laboratory setting. M. S. thesis. Michigan State University, East Lansing, Mich.

Younts, S. M. 1999b. Chapter 3: Differentiation of *Escherichia coli* O157:H7 From non-O157:H7 *E. coli* serotypes using a gas sensor based, computer-controlled detection system. M.S. thesis. Michigan State University, East Lansing, Mich.

Zadik, P. M., P. A. Chapman, and C. A. Siddons. 1993. Use of tellurite for the selection of verocytotoxigenic *Escherichia coli* O157. Journal of Medical Microbiology 39: 155–158.

Zhao, T. , M. P. Doyle, B. G. Harmon, C. A. Brown, P. O. E. Mueller, and A. H. Parks. 1998. Reduction of carriage of enterohemorrhagic *Escherichia coli* O157:H7 in cattle by inoculation with probiotic bacteria. Journal of Clinical Microbiology 36: 641–647.

It is intended that the foregoing description be only illustrative of the present invention and that the present invention be limited only by the hereinafter appended claims.

We claim:

1. An apparatus for detection of at least one volatile product in a sample which comprises:
   (a) a circuit comprising
      (i) one or more gas-detecting transducer means mounted in a confined space for containing the sample which detects the volatile product produced from the sample to produce a first analog signal,
      (ii) a temperature-detecting transducer means mounted in the confined space for containing the sample which detects temperature in the confined space to produce a second analog signal, and
      (iii) a humidity-detecting transducer means mounted in the confined space containing the sample which detects humidity in the confined space to produce a third analog signal;
   (b) an analog to digital conversion means in the circuit for converting the first, second, and third analog signals to digital signals; and
   (c) an acquisition means in the circuit which stores the digital signals resulting from the analog signals in memory as detectable signals and retrieves the detectable signals to provide the detection of the volatile product, the temperature, and the humidity wherein the volatile product in the confined space is detected over time to produce a distinctive signature as a graph of the volatile product in the confined space and wherein the temperature and the humidity in the confined space are detected over time to produce a graph of the temperature and humidity in the confined space.

2. The apparatus of claim 1 wherein the volatile product is produced by a microorganism in the sample.

3. The apparatus of claim 2 wherein the microorganism is pathogenic.

4. The apparatus of claim 2 wherein the microorganism is a pathogenic *Escherichia coli*.

5. The apparatus of claim 2 wherein the microorganism is a Salmonella sp.

6. The apparatus of any one of claims 1 or 2 wherein the volatile product is ammonia.

7. The apparatus of any one of claims 1 or 2 wherein the acquisition means is a computer with a video screen for visualizing the detectable signals.

8. The apparatus of any one of claims 1, 2, 3, 4 or 5 wherein the acquisition means is a computer with a video screen for visualizing the graph.

9. The apparatus of claim 1 wherein the transducer means is mounted in a sealable container as the confined space so that the product from the sample can be detected in the container.

10. The apparatus of claim 9 wherein the transducer means is mounted on a cover for the sealable container.

11. The apparatus of claim 9 wherein at least one resistor is provided in the circuit with the transducer means and wherein the resistor is mounted outside of the container.

12. The apparatus of claim 1 wherein at least one resistor is provided in the circuit with the transducer means to enable reproducible results from the transducer means.

13. The apparatus of claim 1 wherein the conversion means is a 12-bit multiple channel analog to digital converter so that multiple of the product can each be detected from different of the transducer means.

14. The apparatus of claim 1 wherein an artificial neural network is provided in the acquisition means to analyze the detectable signals over time and to recognize a pattern of the volatile product in the sample.

15. A method for detecting a volatile product in a sample which comprises:
   (a) providing an apparatus adjacent the sample which comprises:
      a circuit comprising
         (i) one or more gas-detecting transducer means mounted in a confined space for containing the sample which detects the volatile product produced from the sample to produce a first analog signal,
         (ii) a temperature-detecting transducer means mounted in the confined space for containing the sample which detects temperature in the confined space to produce a second analog signal, and
         (iii) a humidity-detecting transducer means mounted in the confined space containing the sample which detects humidity in the confined space to produce a third analog signal;
      an analog to digital conversion means in the circuit for converting the first, second, and third analog signals to digital signals; and
      an acquisition means in the circuit which stores the digital signals resulting from the analog signals in a memory as detectable signals and retrieves the detectable signals to provide detection of the volatile product, the temperature, and the humidity; and (b) detecting the volatile product produced from the sample in the confined space with the gas-detecting transducer means in the circuit, the temperature in the confined space with the temperature-detecting transducer, and the humidity in the confined space with the humidity-detecting transducer wherein the volatile product in the confined space is detected over time to produce a distinctive signature as a graph of the volatile product in the confined space and wherein the temperature and the humidity in the confined space are detected over time to produce a graph of the temperature and humidity in the confined space.

16. The method of claim 15 wherein the volatile by-product is ammonia which is detected repeatedly over a period of time.

17. The method of claim 16 wherein the ammonia is produced by a microorganism.

18. The method of claim 17 wherein the microorganism is a pathogenic *Escherichia coli*.

19. The method of claim 15 wherein the sample is placed in a sealable container which is then sealed, and wherein the transducer means is adjacent to a food material in a sealed container as the confined space.

20. An apparatus for detection of a volatile by-product produced by a microorganism on a food material which comprises:
(a) a circuit comprising
(i) one or more gas-detecting transducer means mounted in a confined space containing a sample of the food material which detects the by-product produced by the microorganism on the sample to produce a first analog signal,
(ii) a temperature-detecting transducer means mounted in the confined space for containing the sample which detects temperature in the confined space to produce a second analog signal, and
(iii) a humidity-detecting transducer means mounted in the confined space containing the sample which detects humidity in the confined space to produce a third analog signal;
(b) an analog to digital converter means in the circuit for converting the first, second, and third analog signals to digital signals; and
(c) an acquisition means in the circuit which stores from the digital signals resulting from the analog signals in a memory as detectable signals and retrieves the detectable signals to produce the detection of the volatile by-product, the temperature, and humidity wherein the volatile by-product is detected over time to produce a distinctive signature as a graph of the volatile by-product in the confined space and wherein the temperature and the humidity in the confined space are detected over time to produce a graph of the temperature and humidity in the confined space.

21. The apparatus of claim 20 wherein the transducer means detects a fermentation by-product produced by the microorganism.

22. The apparatus of claim 21 wherein the food material is a potato.

23. The apparatus of any one of claims 20, 21, or 22 wherein the acquisition means is in a computer with a video screen for visualizing the detectable signals.

24. The apparatus of claims 20, 21, or 22 wherein the acquisition means is in a computer with a video screen for visualizing the detectable signals and wherein the detectable signals are recorded in a graph.

25. The apparatus of claim 20 wherein the transducer means is mounted in a sealable container so that the volatile by-product can be detected in the container.

26. The apparatus of claim 25 wherein the transducer means is mounted on a cover for the sealable container.

27. The apparatus of claim 20 wherein at least one resistor is provided in the circuit with the transducer means to enable reproducible results from the transducer means.

28. The apparatus of claim 27 wherein at least one resistor is provided in the circuit with the transducer means to enable reproducible results from the transducer means and wherein the resistor is mounted outside of a container for the food material.

29. The apparatus of claim 20 wherein the converter means is a 12-bit multiple channel analog to digital converter so that multiple of the by-product can each be detected from different transducer means.

30. The apparatus of claim 20 wherein an artificial neural network is provided in the acquisition means to analyze the detectable signals over time and to recognize a particular pattern of the volatile by-product produced by the microorganism.

31. A method for detecting a volatile by-product produced by a microorganism on a biological material which comprises:
(a) providing an apparatus for the detection of the volatile by-product produced by the microorganism on the biological material which comprises:
a circuit comprising
(i) one or more gas-detecting transducer means mounted on a container for containing a sample of biological material which detects the volatile by-product produced by the microorganism on the biological material to produce an analog signal,
(ii) a temperature-detecting transducer means mounted in the confined space for containing the biological material which detects temperature in the confined space to produce a second analog signal, and
(iii) a humidity-detecting transducer means mounted in the confined space containing the biological material which detects humidity in the confined space to produce a third analog signal;
an analog to digital converter means in the circuit for converting the first, second, and third analog signals to digital signals; and
an acquisition means in the circuit which stores the digital signals resulting from the analog signals in memory as detectable signals and retrieves the detectable signals to produce detection of the volatile by-product; and
(b) detecting the volatile by-product of the microorganism with the gas-detecting transducer means in the circuit, the temperature with the temperature-detecting transducer in the circuit, and the humidity with the humidity-detecting transducer in the circuit wherein the volatile by-product in the container is detected over time to produce a distinctive signature as a graph of the volatile by-product in the container and wherein the temperature and the humidity in the confined space are detected over time to produce a graph of the temperature and humidity in the confined space.

32. The method of claim 31 wherein the biological material is a food positioned adjacent to the transducer means.

33. The method of claim 32 wherein the volatile by-product is an alcohol.

34. The method of claim 32 wherein the biological material is a potato and the volatile by-product is an alcohol.

35. The method of claim 32 wherein the food material is placed in a sealable container and wherein the transducer means is adjacent to the food material in the sealed container.

* * * * *